US00RE48105E

(19) United States
(12) Reissued Patent
Hung et al.

(10) Patent Number: US RE48,105 E
(45) Date of Reissued Patent: *Jul. 21, 2020

(54) COMPOUNDS FOR THE TREATMENT OF MYCOBACTERIAL INFECTIONS

(71) Applicants: The Broad Institute, Inc., Cambridge, MA (US); The General Hospital Corporation, Boston, MA (US)

(72) Inventors: Deborah Hung, Lexington, MA (US); Sarah Stanley, Berkeley, CA (US); Tomohiko Kawate, Arlington, MA (US); Noriaki Iwase, Yamaguchi (JP); Motohisa Shimizu, Yamaguchi (JP)

(73) Assignees: The Broad Institute, Inc., Cambridge, MA (US); The General Hospital Corporation, Boston, MA (US)

( * ) Notice: This patent is subject to a terminal disclaimer.

(21) Appl. No.: 16/103,823

(22) Filed: Aug. 14, 2018

Related U.S. Patent Documents

Reissue of:
(64) Patent No.: 9,416,121
Issued: Aug. 16, 2016
Appl. No.: 14/227,372
Filed: Mar. 27, 2014

U.S. Applications:
(63) Continuation of application No. PCT/US2012/057913, filed on Sep. 28, 2012.

(60) Provisional application No. 61/540,943, filed on Sep. 29, 2011.

(51) Int. Cl.

| | |
|---|---|
| ***C07D 213/79*** | (2006.01) |
| ***C07D 311/18*** | (2006.01) |
| ***C07D 311/16*** | (2006.01) |
| ***C07D 405/04*** | (2006.01) |
| ***A61K 31/37*** | (2006.01) |
| ***A61K 31/453*** | (2006.01) |
| ***A61K 31/496*** | (2006.01) |
| ***A61K 31/5377*** | (2006.01) |

(52) U.S. Cl.
CPC ..... *C07D 311/16* (2013.01); *A61K 31/37* (2013.01); *A61K 31/453* (2013.01); *A61K 31/496* (2013.01); *A61K 31/5377* (2013.01); *C07D 311/18* (2013.01); *C07D 405/04* (2013.01)

(58) Field of Classification Search
CPC .. C07D 311/16; C07D 311/18; C07D 405/04; A61K 31/5377; A61K 31/496; A61K 31/453; A61K 31/37
See application file for complete search history.

(56) References Cited

U.S. PATENT DOCUMENTS

| | | | |
|---|---|---|---|
| 5,656,644 | A | 8/1997 | Adams et al. |
| 9,416,121 | B2 | 8/2016 | Hung et al. |
| 9,682,064 | B2 | 6/2017 | Hung et al. |
| 2010/0331400 | A1 | 12/2010 | Ho et al. |

FOREIGN PATENT DOCUMENTS

WO 2009/157020 A1 12/2009

OTHER PUBLICATIONS

Kawate, T., et al., "Synthesis and structure-activity relationships of phenyl-substituted coumarins with anti-tubercular that target FadD32," Bioorganic & Medicinal Chemistry Letters, 23: 6052-6059 (2013).
Mashelkar et al. Indian Journal of Chemistry, Section B: Organic Chemistry Including Medicinal Chemistry (2011),50B(3), 315-320.*
Shi et al. Journal of Organic Chemistry (2004), 69(11), 3669-3671.*
Moskvina et 31. Synthesis (2009), (8), 1279-1286.*
Li, Journal of Organic Chemistry (2005), 70(16), 6515-6518.*
Venkatesh et al., J. Pharm. Sci. 89, 145-54 (2000).*
STN Abstrct of KUMGM (University of Kansas Molecular Graphics and Modeling Laboratory), Dec. 19, 2007.*
Wolff, Burger's medicinal Chemistry and Drug Discovery, vol. 1, Principles and Practice, John Wiley & sons, New York, 1997.*
Moskvina et al. Synthesis 2009(8): 1279-1286.*
Ananthan, NIH article 2009 89(5):334-353.*
Stanely et al. ACS Chem. Biol. 2612, 7, 1377-1384.*
Dorwald F. A. Side Reactions in Organic Synthesis, 2005, Wil VCH, Weinheim p. IX of Preface p. 1-15.*
PUBCHEM CID 6540169 (Create: date May 12, 2006) p. 1.
Ananthan, et al., "High Throughput Screening for Inhibitors of *Mycobacterium tuberculosis* H37Rv," Tuberculosis (Edinb). Sep. 2009; 89(5): 334-353. Downloaded from http://www.ncb.inlm.nih.gov/pmc/articles/PMC3255569/.

* cited by examiner

*Primary Examiner* — Dwayne C. Jones
(74) *Attorney, Agent, or Firm* — Elmore Patent Law Group, P.C.; Mahreen Chaudhry Hoda; Carolyn S. Elmore

(57) ABSTRACT

The invention relates to compounds of Formula I or a pharmaceutically acceptable salt, ester or prodrug thereof:

Formula I

19 Claims, No Drawings

COMPOUNDS FOR THE TREATMENT OF MYCOBACTERIAL INFECTIONS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

This application is a continuation of International Application No. PCT/US2012/057913, which designated the United States and was filed on Sep. 28, 2012, published in English, which claims the benefit of U.S. Provisional Application No. 61/540,943, filed on Sep. 29, 2011. The entire teachings of the above applications are incorporated herein by reference.

BACKGROUND

Tuberculosis (TB) is a disease caused by the bacterium Mycobacterium tuberculosis (Mtb), and is spread from person to person through the air. It is estimated that one-third of world's population are latently infected by Mtb. Despite the availability of effective anti-TB drugs, such as isoniazide and rifampin, TB is still one of the world's deadliest diseases. According to World Health Organization, there were 9.4 million new TB cases and 1.7 million people died from TB in 2009. [Global tuberculosis control: WHO report 2010.WHO//HTM/TB/2010.7]. Development of new agents that reduce the duration and complexity of current therapies, as well as effectively kill emerging resistant mutants, multiple drug resistant TB and extensively drug resistant TB, would have a major impact on the TB therapy.

SUMMARY OF THE INVENTION

The invention relates to compounds of Formula I or a pharmaceutically acceptable salt, ester or prodrug thereof:

Formula I

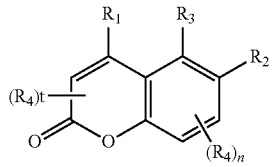

Wherein, n is 0, 1, or 2;

t is 0 or 1;

$R_1$ is hydrogen, halogen, —$OR_{20}$, —$SR_{20}$, —$NR_{20}R_{21}$, —$CF_3$, —CN, —$NO_2$, —$N_3$, —C(O)$OR_{20}$, —C(O)$R_{20}$, —C(O)$NR_{20}R_{21}$, acyl, alkyl, substituted alkyl, alkenyl, substituted alkenyl, alkynyl, substituted alkynyl, aryl, substituted aryl, heteroaryl or substituted heteroaryl;

Wherein each $R_{20}$ and $R_{21}$ is independently hydrogen, halogen, alkyl, aliphatic, substituted aliphatic, aryl or substituted aryl;

$R_3$ is hydrogen, halogen, —$OR_{20}$, —$SR_{20}$, —$NR_{20}R_{21}$, —$CF_3$, —CN, —$NO_2$, —$N_3$, —C(O)$OR_{20}$, —C(O)$R_{20}$, —C(O)$NR_{20}R_{21}$, acyl, alkyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl;

Each $R_4$ is independently selected from hydrogen, halogen, —$OR_{20}$, —$SR_{20}$, —$NR_{20}R_{21}$, —$CF_3$, —CN, —$NO_2$, —$N_3$, —C(O)$OR_{20}$, —C(O)$R_{20}$, —C(O)$NR_{20}R_{21}$, acyl, alkyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl; alternatively two $R_4$ groups together with the atoms to which they are attached and any intervening atoms may form an additional optionally substituted, 3, 4, 5, 6 or 7 membered ring;

$R_2$ is aryl, substituted aryl, heterocyclic, substituted heterocyclic, alkyl substituted with aryl, alkenyl substituted with aryl, alkynyl substituted aryl, —$[C(R_{20})(R_{21})]_a$-Cy, —$[C(R_{20})(R_{21})]_a$=$[C(R_{20})(R_{21})]_a$-Cy, —O$[C(R_{20})(R_{21})]_a$-Cy, —S$[C(R_{20})(R_{21})]_a$-Cy, or —N($R_{20}$)$[C(R_{20})(R_{21})]_a$-Cy;

Wherein Cy is aryl, substituted aryl, heterocyclic, substituted heterocyclic, carbocyclic or substituted carbocyclic;

Each a is independently 0, 1, 2, 3, 4, 5, 6, 7, 8, 9, 10, 11, 12, 13, 14, 15, 16, 17, 18, 19 or 20.

The invention further relates to the use of a compound of Formula I in the manufacture of a medicament. The invention further relates to the use of a compound of Formula I for the treatment of a bacterial infection, in particular, mycobacterial infection. The compounds of the invention can be used for anti-mycobacterial activity against clinically sensitive as well as resistant strains of Mycobacterium tuberculosis. Compounds of Formula I are useful for the treatment of mycobacterial diseases, particularly those caused by pathogenic mycobacteria.

DETAILED DESCRIPTION OF THE INVENTION

The invention relates to compounds of Formula I or a pharmaceutically acceptable salt, ester of prodrug thereof:

Formula I

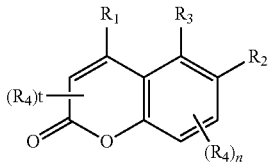

Wherein, n is 0, 1, or 2;

t is 0 or 1;

$R_1$ is hydrogen, halogen, —$OR_{20}$, —$SR_{20}$, —$NR_{20}R_{21}$, —$CF_3$, —CN, —$NO_2$, —$N_3$, —C(O)$OR_{20}$, —C(O)$R_{20}$, —C(O)$NR_{20}R_{21}$, —S(O)$R_{20}$, —S(O)$NR_{20}$, —S(O)$_2R_{20}$, acyl, alkyl, substituted alkyl, alkenyl, substituted alkenyl, alkynyl, substituted alkynyl, aryl, substituted aryl, heteroaryl or substituted heteroaryl;

Wherein each $R_{20}$ and $R_{21}$ is independently hydrogen, halogen, alkyl, aliphatic, substituted aliphatic, aryl or substituted aryl;

$R_3$ is hydrogen, halogen, —$OR_{20}$, —$SR_{20}$, —$NR_{20}R_{21}$, —$CF_3$, —CN, —$NO_2$, —$N_3$, —C(O)$OR_{20}$, —C(O)$R_{20}$, —C(O)$NR_{20}R_{21}$, acyl, alkyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl;

Each $R_4$ and $R_9$ is independently selected from hydrogen, halogen, —$OR_{20}$, —$SR_{20}$, —$NR_{20}R_{21}$, —$CF_3$, —CN, —$NO_2$, —$N_3$, —C(O)$OR_{20}$, —C(O)$R_{20}$, —C(O)$NR_{20}R_{21}$, acyl, alkyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl; alternatively two $R_4$ groups together with the atoms to which they are attached and any intervening atoms may form an additional optionally substituted, 3, 4, 5, 6 or 7 membered ring;

$R_2$ is aryl, substituted aryl, heterocyclic, substituted heterocyclic, —$[C(R_{20})(R_{21})]_a$-Cy, —$[C(R_{20})(R_{21})]_a[C(R_{20})(R_{21})]_a$-Cy, —$O[C(R_{20})(R_{21})]_a$-Cy, —$S[C(R_{20})(R_{21})]_a$-Cy, —$N(R_{20})[C(R_{20})(R_{21})]_b$-Cy;

Wherein Cy is aryl, substituted aryl, heterocyclic, substituted heterocyclic, carbocyclic or substituted carbocyclic;

Each a is independently 0, 1, 2, 3, 4, 5, 6, 7, 8, 9, 10, 11, 12, 13, 14, 15, 16, 17, 18, 19 or 20.

In a preferred embodiment, $R_1$ is alkyl, aryl, substituted aryl, heteroaryl or substituted heteroaryl.

In a preferred embodiment, $R_2$ is selected from:

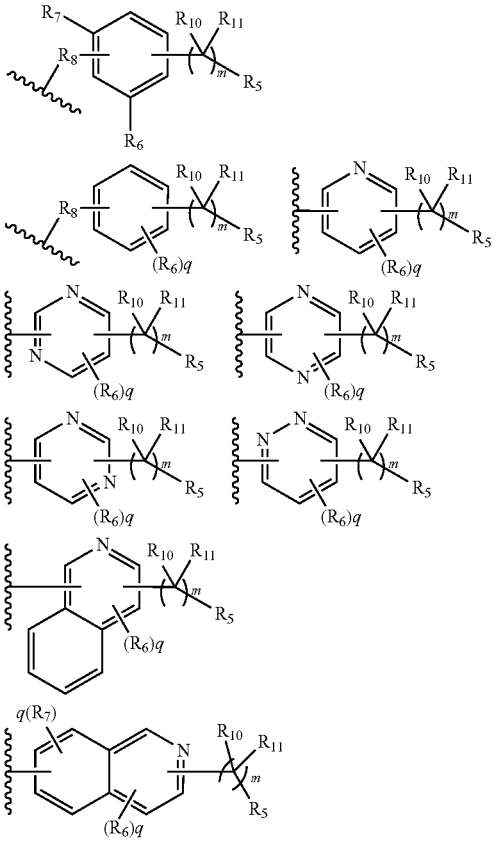

-continued

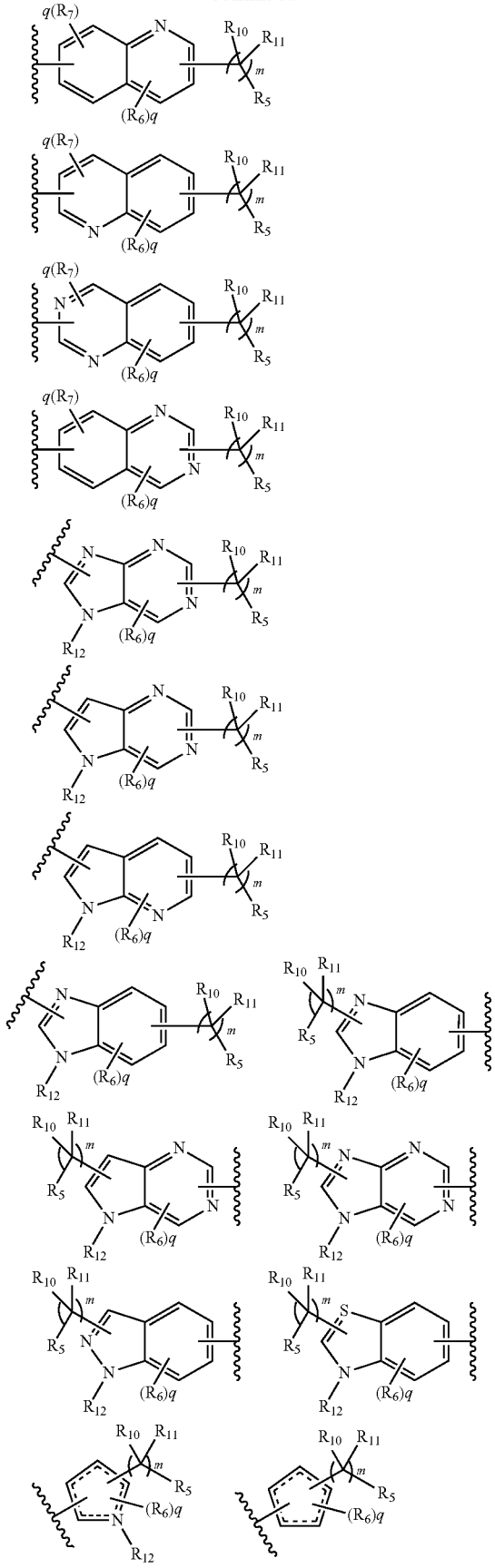

-continued

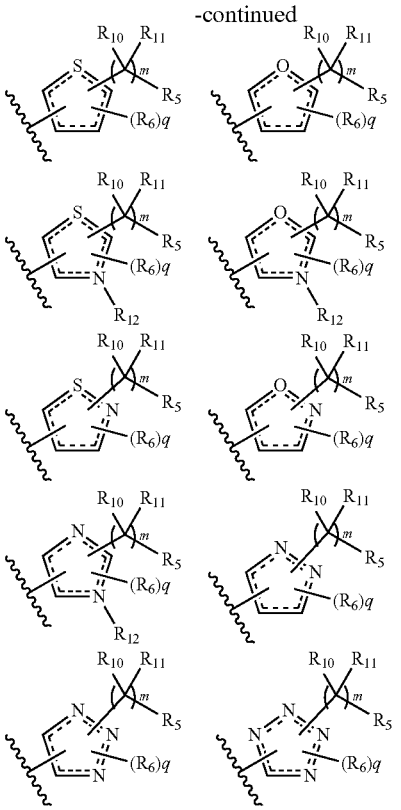

Wherein m is 0, 1, 2, 3, 4, 5, 6, 7, 8, 9, 10, 11 or 12;

q is 0, 1, 2, 3 or 4;

Each $R_6$, $R_7$, $R_{10}$ and $R_{11}$ is independently selected from absent, hydrogen, halogen, —$OR_{20}$, —$SR_{20}$, —$NR_{20}R_{21}$, —$CF_3$, —CN, —$NO_2$, —$N_3$, —OH, —SH, —C(O)$OR_{20}$, —C(O)$R_{20}$, —C(O)$NR_{20}R_{21}$, —S(O)$R_{20}$, —S(O)$NR_{20}$, —S(O)$_2R_{20}$, acyl, alkyl, alkenyl, alkoxy, oxo, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl; alternatively two $R_{10}$ and $R_{11}$ groups together with the atoms to which they are attached and any intervening atoms may form an additional optionally substituted, 3, 4, 5, 6 or 7 membered ring;

$R_5$ is selected from absent, hydrogen, halogen, —$NR_{20}R_{21}$, $OR_{20}$, $SR_{20}$, —$CF_3$, —CN, —$NO_2$, —$N_3$, —C(O)$OR_{20}$, —C(O)$R_{20}$, —C(O)$NR_{20}R_{21}$, —S(O)$R_{20}$, —S(O)$NR_{20}$, —S(O)$_2R_{20}$, alkyl, substituted alkyl, aryl, substituted aryl, heterocyclic and substituted heterocyclic;

Wherein when $R_{21}$ is hydrogen, $R_{20}$ is other than H, $CH_3$ or —C(O)$CH_3$;

$R_8$ is absent, —O—, —S—, —$NR_{10}$—, —C(O)—, —C(O)O—, alkyl, substituted alkyl, alkenyl, substituted alkenyl, alkynyl or substituted alkynyl alkynyl.

In a preferred embodiment, $R_5$ is $NR_{22}R_{23}$;

Wherein $R_{22}$ is selected from hydrogen, $C_1$-$C_{20}$ alkyl, substituted $C_1$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_3$-$C_{20}$ cycloalkyl; substituted $C_3$-$C_{20}$ cycloalkyl;

Wherein $R_{23}$ is selected from absent, $C_2$-$C_{20}$ alkyl, substituted $C_2$-$C_{20}$ alkyl, $C_2$-$C_{20}$ alkenyl, substituted $C_2$-$C_{20}$ alkenyl, $C_2$-$C_{20}$ alkynyl, substituted $C_2$-$C_{20}$ alkynyl, $C_3$-$C_{20}$ cycloalkyl; substituted $C_3$-$C_{20}$ cycloalkyl;

Alternatively $R_{22}$ and $R_{23}$ together with the nitrogen atom to which they are attached may form an additional optionally substituted, 3, 4, 5, 6 or 7 membered ring;

Wherein when $R_{22}$ is hydrogen, $R_{23}$ is other than —C(O)$CH_3$.

In a more preferred embodiment, $R_5$ is selected from:

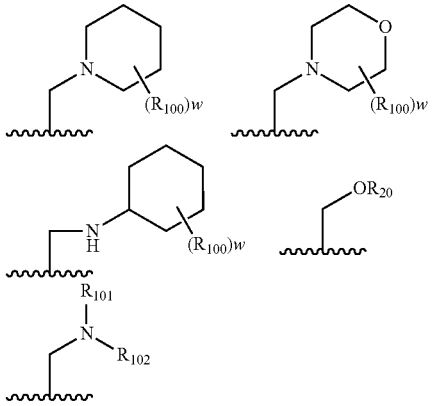

Wherein w is 0, 1, 2, 3, 4, 5, 6, 7, 8, 9 or 10;

$R_{100}$ is hydrogen, halogen, —$NR_{20}R_{21}$, $OR_{20}$, $SR_{20}$, —$CF_3$, —CN, —$NO_2$, —$N_3$, —C(O)$OR_{20}$, —C(O)$R_{20}$, —C(O)$NR_{20}R_{21}$, —S(O)$R_{20}$, —S(O)$NR_{20}$, —S(O)$_2R_{20}$, alkyl, substituted alkyl, aryl, substituted aryl, heterocyclic or substituted heterocyclic;

Each $R_{101}$ and $R_{102}$ is independently selected from hydrogen, alkyl, substituted alkyl, aryl, substituted aryl, heterocyclic or substituted heterocyclic.

In a preferred embodiment, the invention relates to a compound selected from Table A:

TABLE A

| No | Structure | $IC_{90}$ (μM) |
|---|---|---|
| 1 | 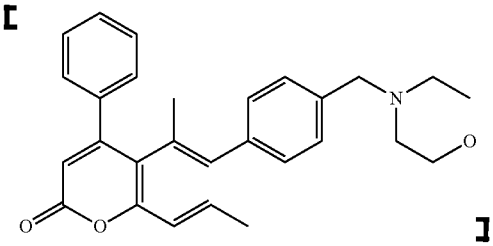 | I |

TABLE A-continued
| No | Structure | $IC_{90}$ (μM) |
|---|---|---|
| | 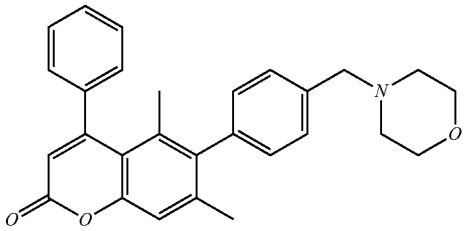 5,7-dimethyl-6-(4-(morpholinomethyl)phenyl)-4-phenyl-2H-chromen-2-one | |
| 2 | 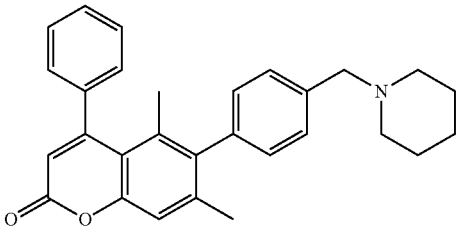 5,7-dimethyl-4-phenyl-6-(4-(piperidin-1-ylmethyl)phenyl)-2H-chromen-2-one | II |
| 3 | 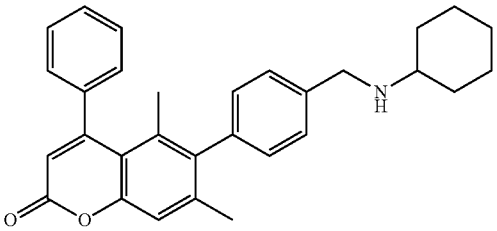 6-(4-((cyclohexylamino)methyl)phenyl)-5,7-dimethyl-4-phenyl-2H-chromen-2-one | I |
| 4 | 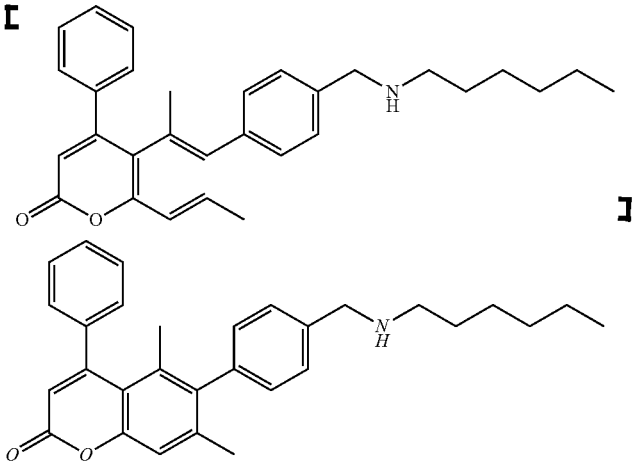 5,7-dimethyl-6-(4-((hexylamino)methyl)phenyl)-4-phenyl-2H-chromen-2-one | I |

TABLE A-continued

| No | Structure | $IC_{90}$ (μM) |
|---|---|---|
| 5 | 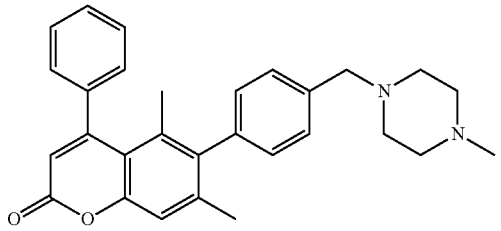 <br>5,7-dimethyl-6-(4-((4-methylpiperazin-1-yl)methyl)phenyl)-4-phenyl-2H-chromen-2-one | I |
| 6 | 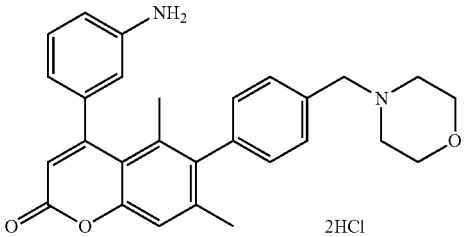 <br>4-(3-aminophenyl)-5,7-dimethyl-6-(4-(morpholinomethyl)phenyl)-2H-chromen-2-one hydrochloride | I |
| 7 | 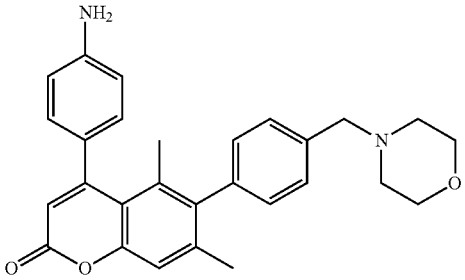 <br>4-(4-aminophenyl)-5,7-dimethyl-6-(4-(morpholinomethyl)phenyl)-2H-chromen-2-one | II |
| 8 | 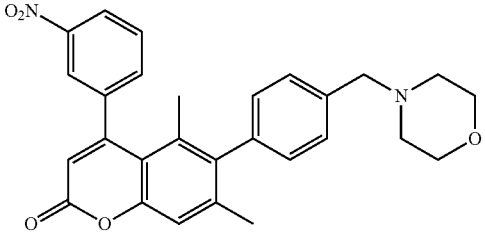 <br>5,7-dimethyl-6-(4-(morpholinomethyl)phenyl)-4-(3-nitrophenyl)-2H-chromen-2-one | I |
| 9 | 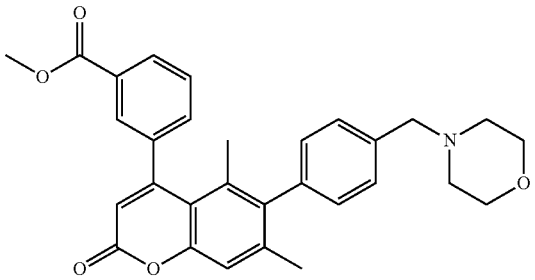 <br>methyl 3-(5,7-dimethyl-6-(4-(morpholinomethyl)phenyl)-2-oxo-2H-chromen-4-yl)benzoate | III |

TABLE A-continued
| No | Structure | $IC_{90}$ (μM) |
|---|---|---|
| 10 | 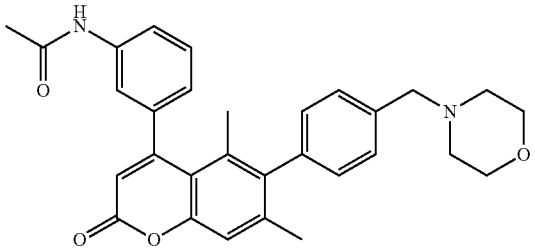 N-(3-(5,7-dimethyl-6-(4-(morpholinomethyl)phenyl)-2-oxo-2H-chromen-4-yl)phenyl)acetamide | II |
| 11 | 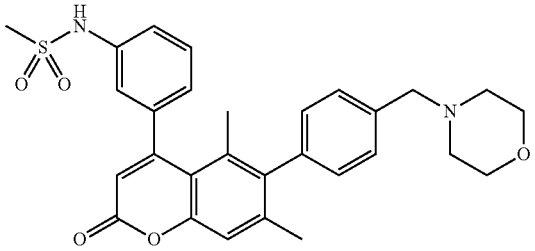 N-(3-(5,7-dimethyl-6-(4-(morpholinomethyl)phenyl)-2-oxo-2H-chromen-4-yl)phenyl)methanesulfonamide | III |
| 12 | 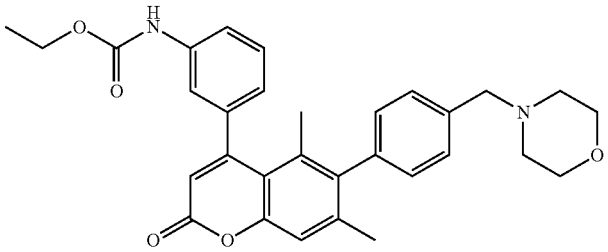 ethyl (3-(5,7-dimethyl-6-(4-(morpholinomethyl)phenyl)-2-oxo-2H-chromen-4-yl)phenyl)carbamate | II |
| 13 | 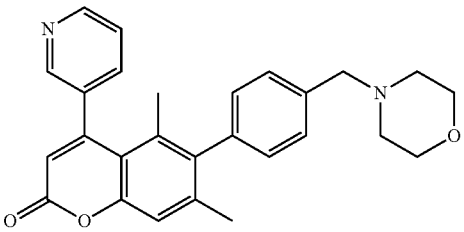 5,7-dimethyl-6-(4-(morpholinomethyl)phenyl)-4-(pyridin-3-yl)-2H-chromen-2-one | I |
| 14 | 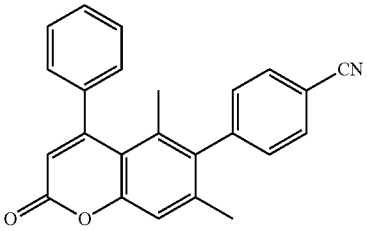 | IV |

TABLE A-continued
| No | Structure | $IC_{90}$ (μM) |
|---|---|---|
| 15 | 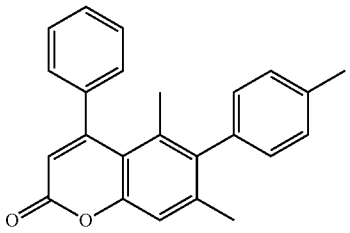 | II |
| 16 | 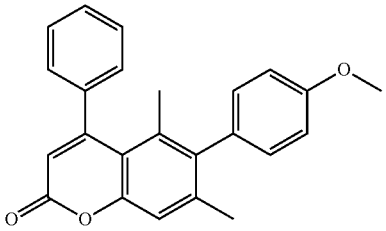 | IV |
| 17 | 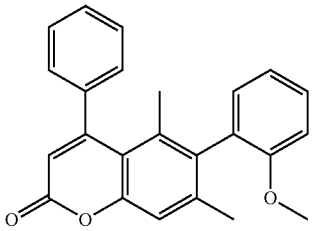 | NA |
| 18 | 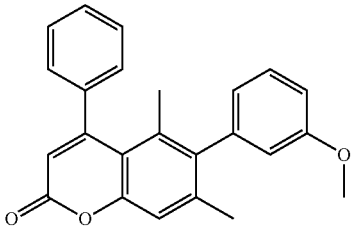 | II |
| 19 | 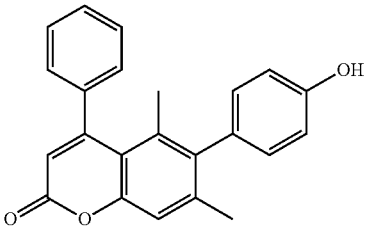 | IV |
| 20 | 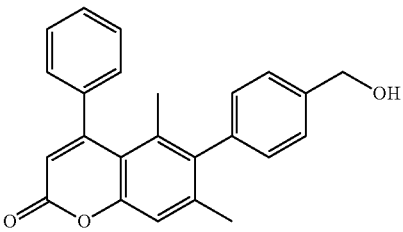 | I |

TABLE A-continued
| No | Structure | $IC_{90}$ (μM) |
|---|---|---|
| 21 | 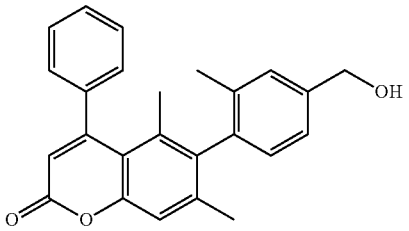 | II |
| 22 | 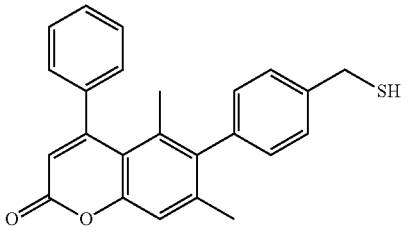 | IV |
| 23 | 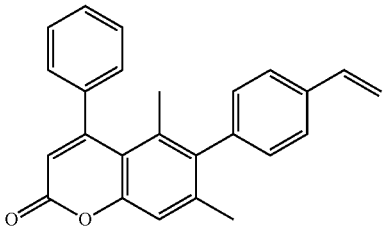 | IV |
| 24 | 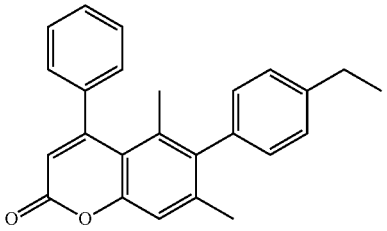 | IV |
| 25 | 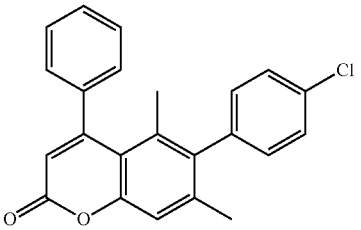 | III |
| 26 | 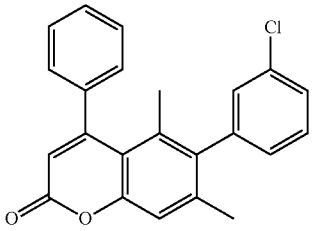 | IV |

TABLE A-continued
| No | Structure | $IC_{90}$ (μM) |
|---|---|---|
| 27 | 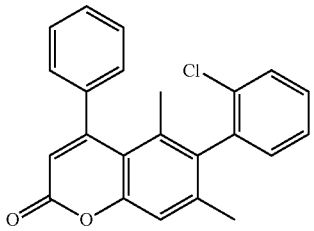 | II |
| 28 | 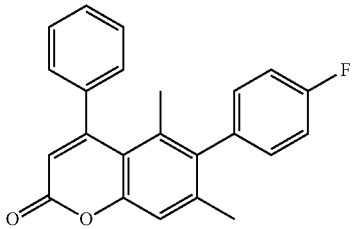 | II |
| 29 | 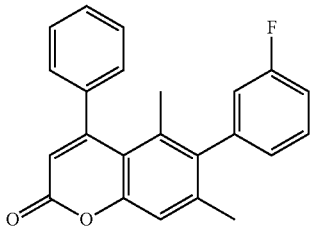 | II |
| 30 | 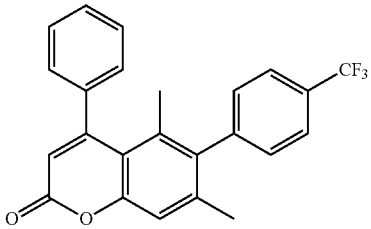 | II |
| 31 | 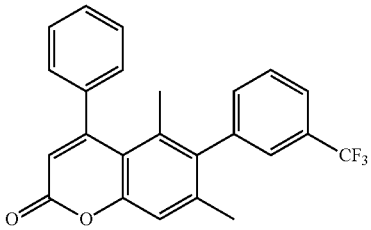 | NA |
| 32 | 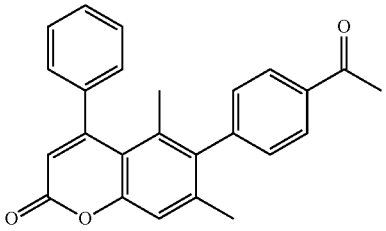 | IV |

TABLE A-continued
| No | Structure | $IC_{90}$ (μM) |
|---|---|---|
| 33 | 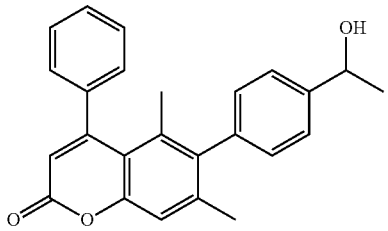 | I |
| 34 | 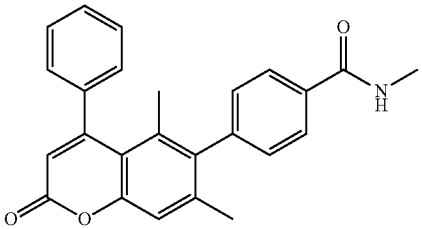 | I |
| 35 | 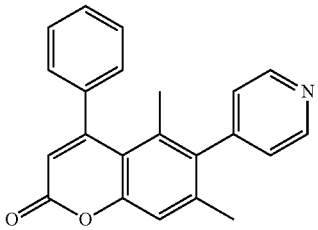 | I |
| 36 | 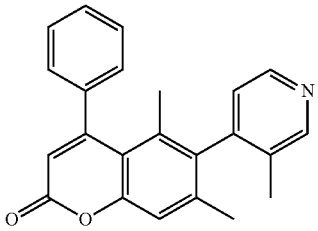 | II |
| 37 | 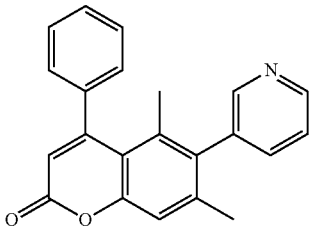 | III |
| 38 | 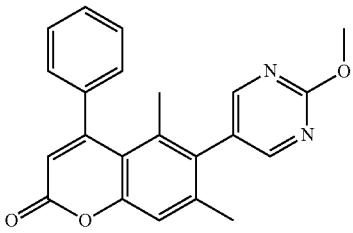 | NA |

TABLE A-continued
| No | Structure | $IC_{90}$ (μM) |
|---|---|---|
| 39 | 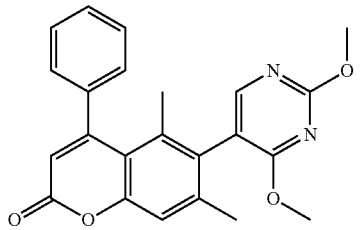 | II |
| 40 | 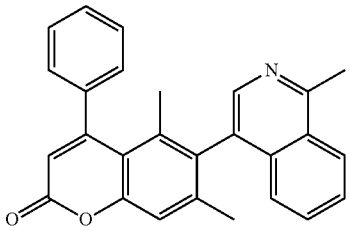 | NA |
| 41 | 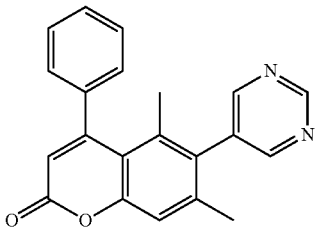 | I |
| 42 | 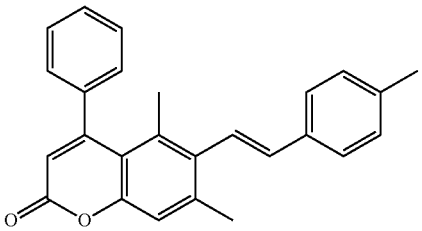 | III |
| 43 | 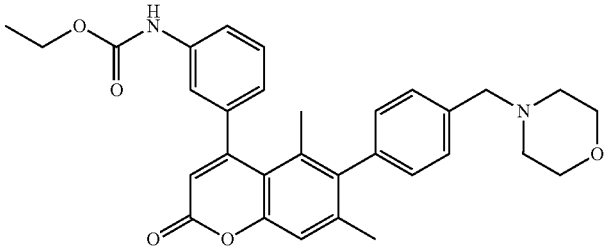 | NA |
| 44 | 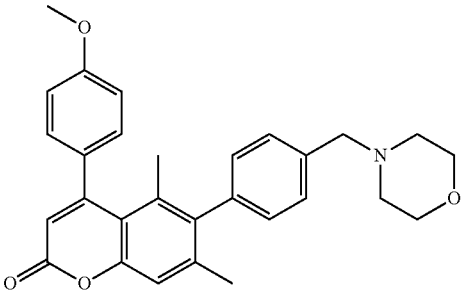 | NA |

TABLE A-continued
| No | Structure | $IC_{90}$ (μM) |
|---|---|---|
| 45 | 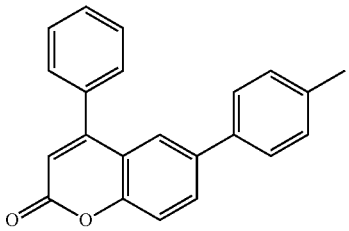 | IV |
| 46 | 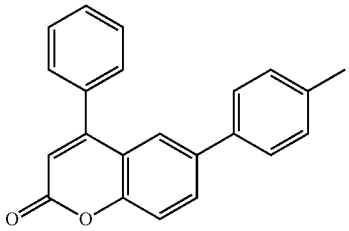 | NA |
| 47 | 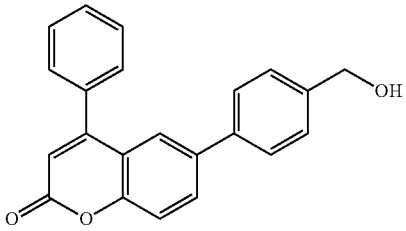 | IV |
| 48 | 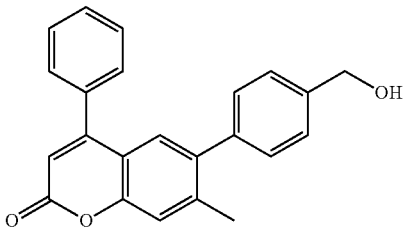 | III |
| 49 | 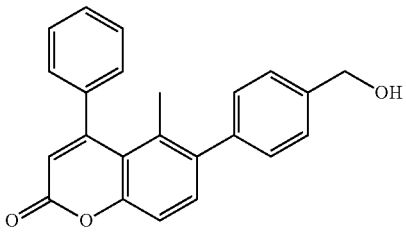 | III |
| 50 | 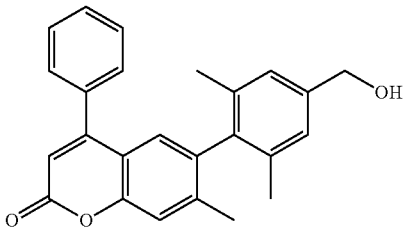 | IV. |

The antitubercular activity of Compounds 1-50 was evaluated against Mtb strain H37Rv. The inhibitory activity ($IC_{90}$) of the compounds is reported in Table A. The inhibitory activity is characterized based on the following scale:

I=0.001 μM-10 μM
II=10 μM-50 μM
III=50 μM-100 μM
IV=>100 μM
NA=No Activity

The invention further relates to the use of a compound of Formula I for the treatment of a mycobacterial infection. The compounds of the invention can be used for anti-mycobacterial activity against mycobacterium infection, in particular against infection caused by resistant strains of mycobacterium tuberculosis. Compounds of Formula I are useful for the treatment of mycobacterial diseases, particularly those caused by pathogenic mycobacteria.

The invention further relates to the use of a compound of Formula I in the manufacture of a medicament. The invention further relates to combination therapy using compounds of Formula I with antibacterial agents, in particular anti-mycobacterial agents. The compounds of Formula I can be combined with antibacterial agents such as rifampicin, rifampin, isoniazid, pyrazinamide, amikacin, ethionamide, moxifloxacin, ethambutol, streptomycin, para-aminosalicylic acid, cycloserine, capreomycin, kanamycin, thiacetazone, PA-824, quinolones/fluoroquinolones such as for example ofloxacin, ciprofloxacin, sparfloxacin; macrolides such as for example clarithromycin, clofazimine, amoxycillin with clavulanic acid, rifamycins, rifabutin, rifapentine.

The following schemes represent general protocols for synthesis of compounds of Formula I:

scheme 1

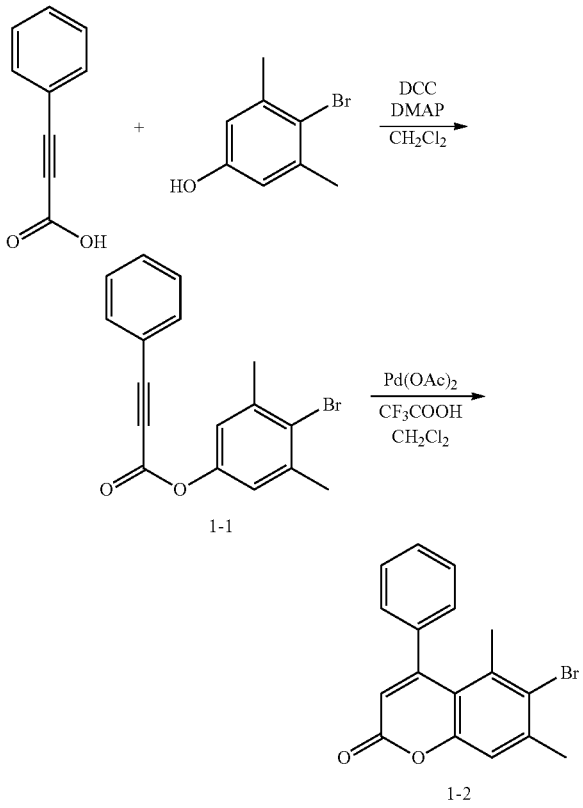

-continued

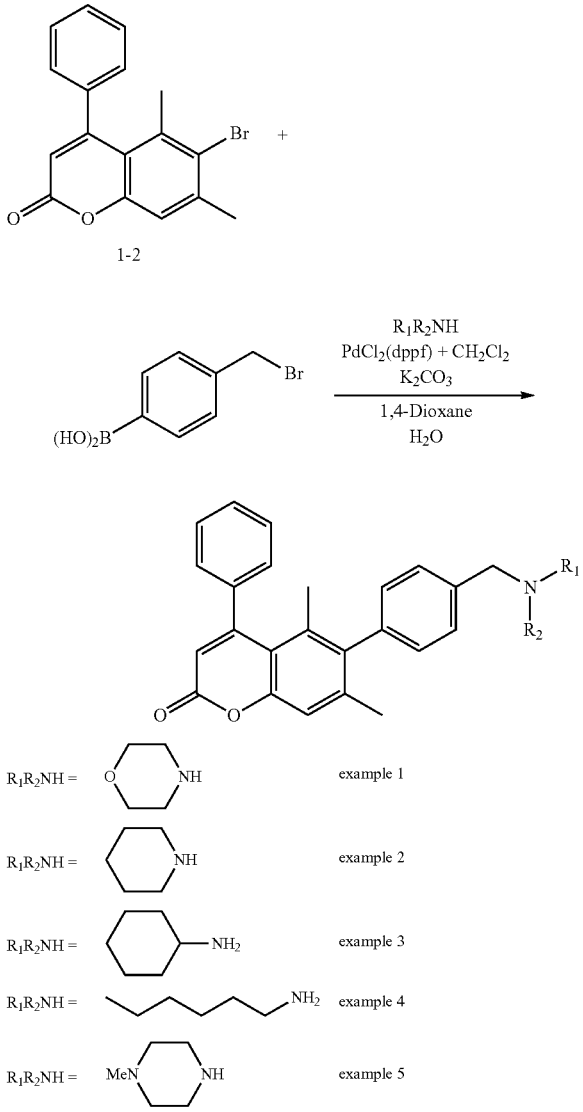

scheme 2

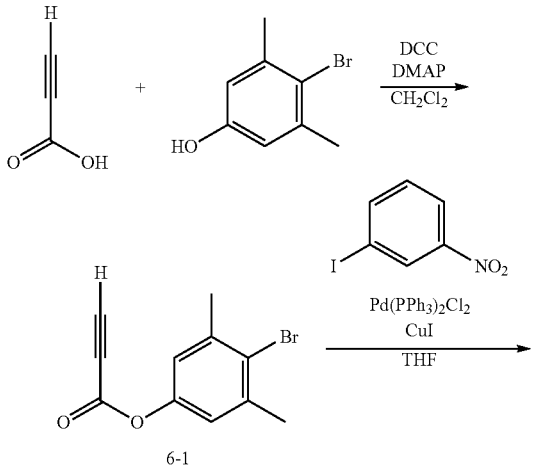

-continued
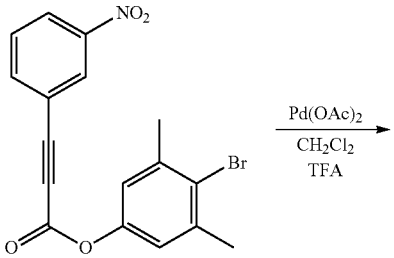
6-2
$Pd(OAc)_2$
$CH_2Cl_2$
TFA
scheme 3
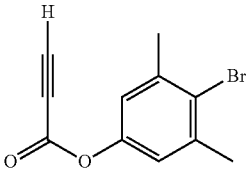
6-1
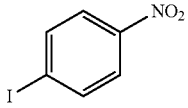
$Pd(PPh_3)_2Cl_2$
CuI
THF
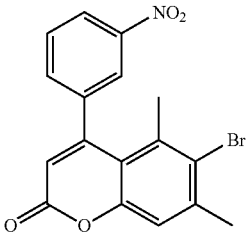
6-3
Fe
AcOH
EtOH
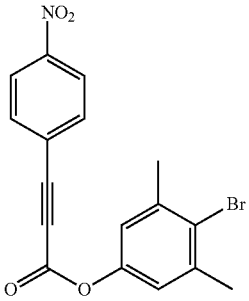
7-1
$Pd(OAc)_2$
$CH_2Cl_2$
TFA
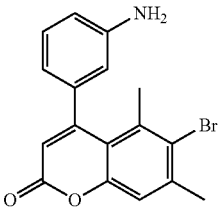
6-4
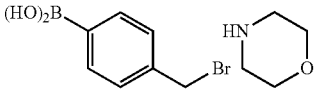
$PdCl_2(dppf) + CH_2Cl_2$
$K_2CO_3$
1,4-Dioxane
$H_2O$
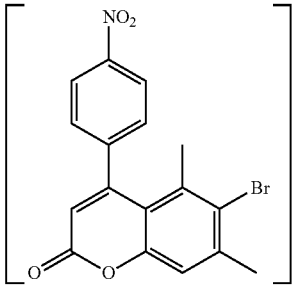
7-2
Fe
AcOH
EtOH
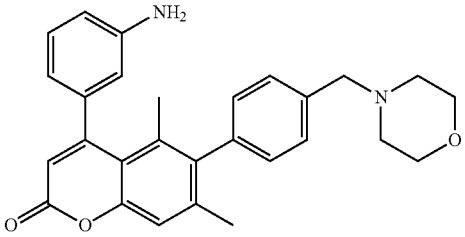
6-5
cHCl
TBME
EtOH
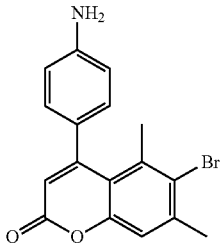
7-3
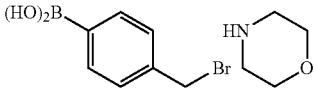
$PdCl_2(dppf) + CH_2Cl_2$
$K_2CO_3$
1,4-Dioxane
$H_2O$
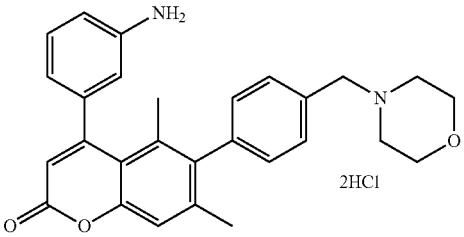
example 6
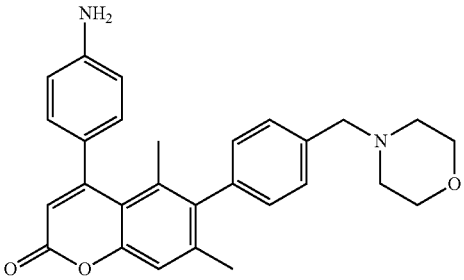
example 7 scheme 4
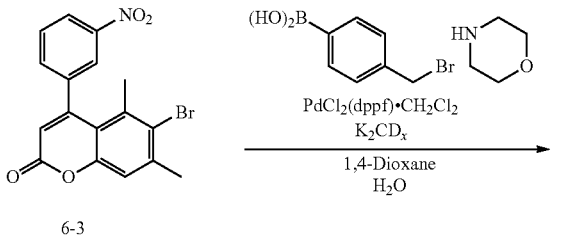
scheme 5
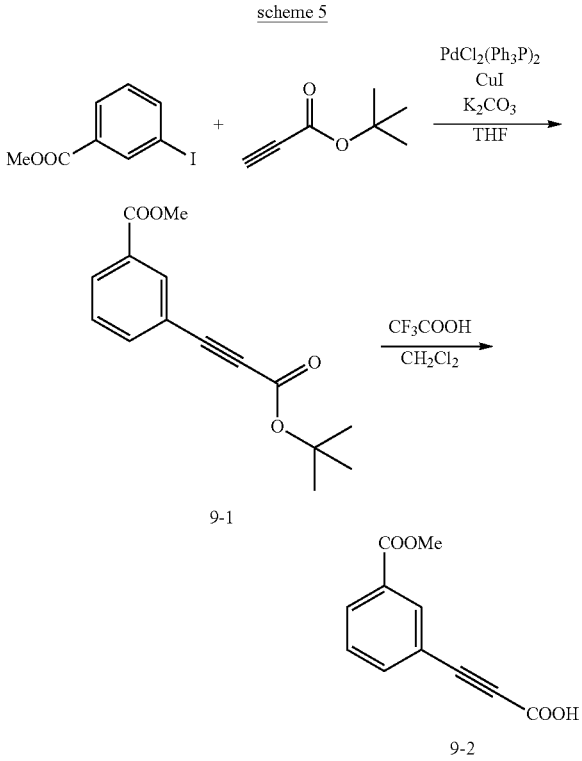
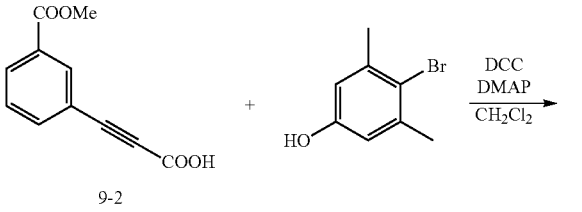
-continued
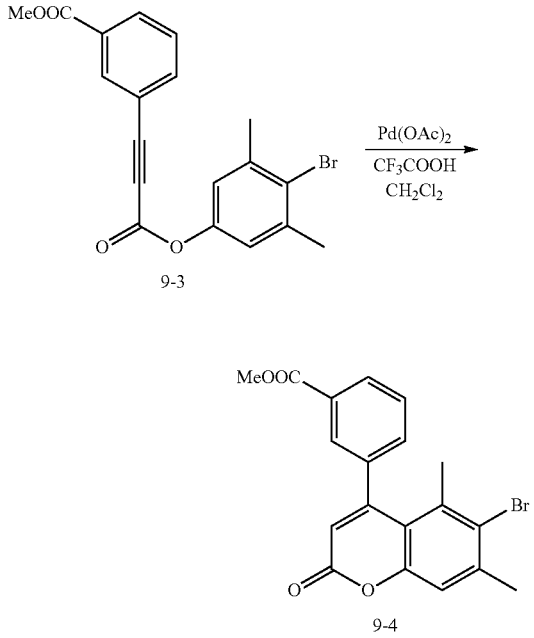
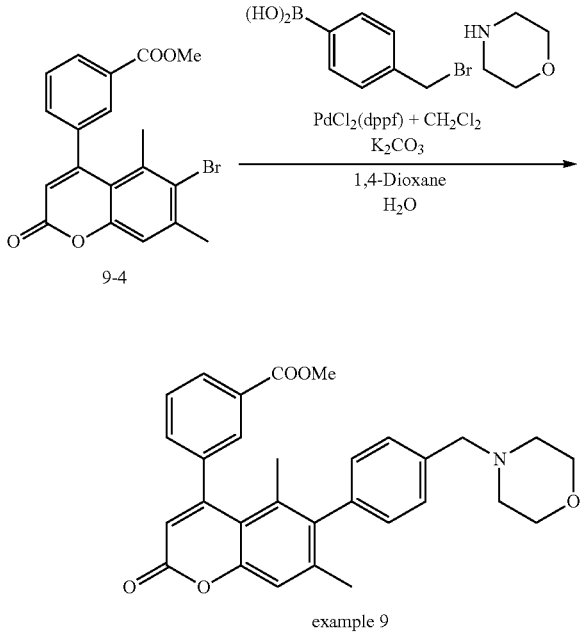
scheme 6
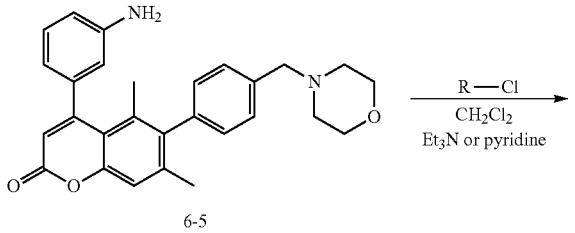

-continued

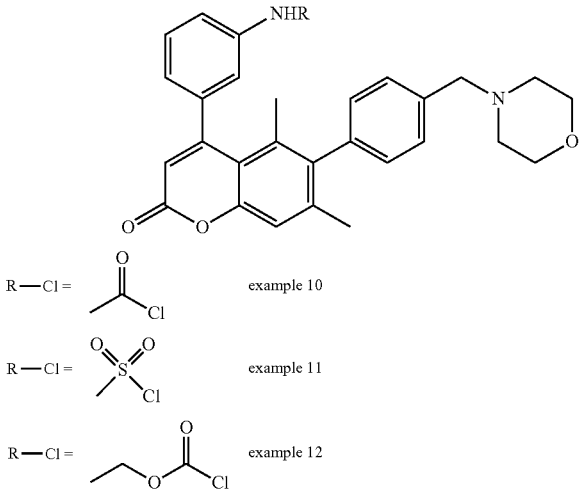

scheme 7

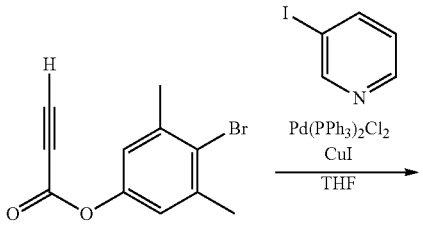

6-1

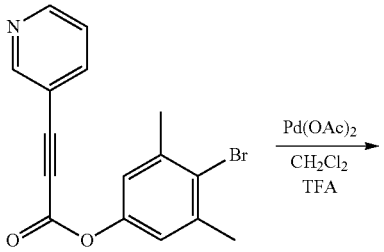

13-1

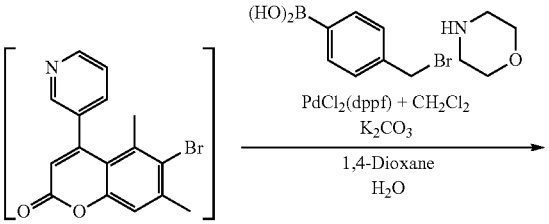

13-2

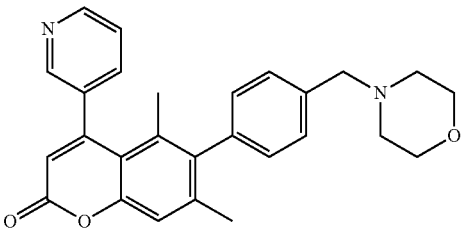

example 13 scheme 8

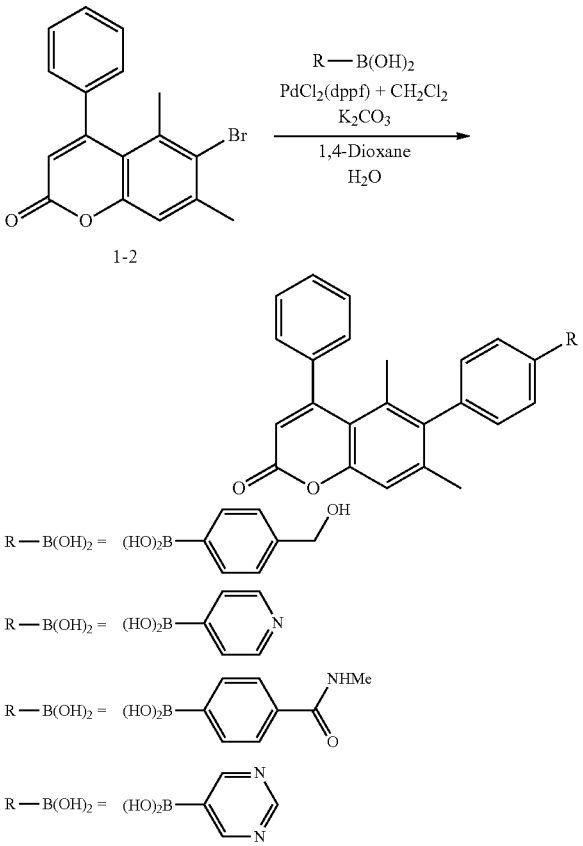

1-2

ABBREVIATIONS

Abbreviations which may appear in the synthetic schemes and examples are:

Ac for acetyl;
Alloc for allyloxycarbonyl;
Boc for tert-butoxycarbonyl;
DCC for N,N'-dicyclohexylcarbodiimide;
DCM for dichloromethane;
DMAP for 4-(dimethylamino)pyridine;
DMF for dimethyl formamide;
DMSO for dimethyl sulfoxide;
Dppf for 1,1'-bis)diphenylphosphino)ferrocene;
EtOAc for ethyl acetate;
EtOH for ethanol;
iPr for isopropyl;
IPA for isopropyl alcohol;
MeOH for methanol;
TBME for tert-butyl methyl ether;
TEA for triethylamine;
TFA for trifluoroaetic acid; and
THF for tetrahydrofuran.

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond)

or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means an aromatic system containing one, two or three rings wherein such rings may be attached together in a pendent manner or may be fused. The term "aryl" embraces aromatic radicals such as phenyl, naphthyl, tetrahydronaphthyl, indane furanyl, quinazolinyl, pyridyl and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H- 1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms "alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound" "drug", and "prodrug" as used herein all include pharmaceutically acceptable salts, co-crystals, solvates, hydrates, polymorphs, enantiomers, diastereoisomers, racemates and the like of the compounds, drugs and prodrugs having the formulas as set forth herein.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread of disease, preventing occurrence or recurrence of disease, delay or slowing of disease progression, amelioration of the disease state, and remission (whether partial or total).

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha-(α), beta-(β) and gamma-(γ) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is parenteral administration by injection.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® or OMEGA-VEN®, or solution, in a nontoxic parenterally acceptable diluent or solvent, for example, as a solution in 1,3-butanediol. INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acid such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics is known in the art (see, for example U.S. Pat. No. 5,767,068 to VanDevanter et al., U.S. Pat. No. 5,508,269 to Smith et al., and WO 98/43650 by Montgomery).

EXAMPLES

Example 1

5,7-Dimethyl-6-(4-(morpholinomethyl)phenyl)-4-phenyl-2H-chromen-2-one example 1

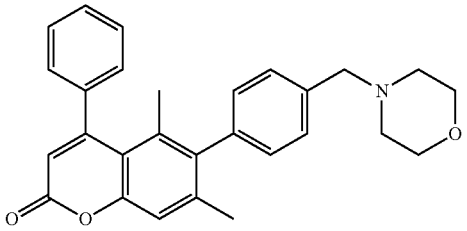

4-Bromo-3,5-dimethylphenyl 3-phenylpropiolate (1-1)

1-1

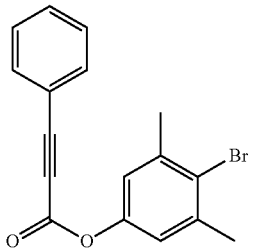

To a stirring mixture of 3-phenylpropiolic (6579 mg, 45.00 mmol), 4-bromo-3,5-dimethylphenol (6032 mg, 30.0 mmol) and 4-(dimethylamino)pyridine (370 mg, 3.0 mmol) in dichloromethane (50 mL) was added a solution of DCC (7442 mg, 36.00 mmol) in dichloromethane (30 mL) under ice-cooling. The mixture was stirred under ice-cooling and slowly warmed up to room temperature. After stirred for 9 h, the mixture was filtered through a pad of Celite and the filtrate was evaporated to dryness. The residue was chromatographed on a silica gel (chloroform:hexanes=3:2) to give the title compound 1-1 (9849 mg, 100% yield) as a pale yellow oil.

$^1$H NMR (300 MHz, $CDCl_3$) δ 7.70-7.56 (m, 1H), 7.54-7.45 (m, 1H), 7.45-7.34 (m, 1H), 6.93 (s, 1H), 2.43 (s, 3H).

6-Bromo-5,7-dimethyl-4-phenyl-2H-chromen-2-one (1-2)

1-2

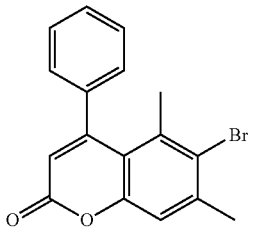

To a stirring solution of 4-bromo-3,5-dimethyl-phenyl 3-phenylpropiolate (1-1) (9839 mg, 30.00 mmol) in dichloromethane (15 mL) and trifluoroacetic acid (45 mL) was added palladium acetate (350 mg, 1.60 mmol) under ice-cooling. After stirred for 2 h under ice-cooling, the mixture was diluted with 1,2-dichloroethane and evaporated to dryness. The residue was chromatographed on a silica gel (chloroform:hexanes=1:1-3:2) to give the title compound 1-2 (7581 mg, 77% yield) as a dark yellow solid.

$^1$H NMR (300 MHz, $CDCl_3$) δ 7.54-7.39 (m, 3H), 7.35-7.24 (m, 2H), 7.19 (s, 1H), 6.26 (s, 1H), 2.51 (s, 3H), 1.95 (s, 3H).

$^{13}$C NMR (75 MHz, $CDCl_3$) δ 160.00, 156.21, 153.78, 142.84, 139.72, 137.02, 129.24, 129.09, 127.30, 125.93, 117.59, 117.03, 25.02, 24.93.

5,7-Dimethyl-6-(4-(morpholinomethyl)phenyl)-4-phenyl-2H-chromen-2-one (example 1)

A mixture of 6-bromo-5,7-dimethyl-4-phenyl-2H-chromen-2-one (1-2) (99 mg, 0.30 mmol), 4-(bromomethyl) phenylboronic acid (97 mg, 0.45 mmol), morpholine (39 μL, 0.45 mmol), potassium carbonate (70 mg, 0.51 mmol) and $Pd(dppf)Cl_2.CH_2Cl_2$ (25 mg, 0.030 mmol) in a mixture of 1,4-dioxane and water (9:1, 3 mL) was stirred at 130° C. for 30 min under microwave irradiation. After cooled to room temperature, the mixture was diluted with ethyl acetate, filtered through a pad of Celite. The filtrate was washed with water and brine and dried over sodium sulfate. Evaporation of the solvents give a residue, which was chromatographed on silica gel (EtOAc:hexanes=1:1-2:1) to give the title compound 1 (114 mg, 89% yield) as a light brown solid.

$^1$H NMR (300 MHz, $CDCl_3$) δ 7.45-7.27 (m, 7H), 7.21 (s, 1H), 7.00 (d, J=8.0, 2H), 6.24 (s, 1H), 3.78-3.64 (m, 4H), 3.52 (s, 2H), 2.51-2.38 (m, 4H), 2.07 (s, 3H), 1.48 (s, 3H).

Example 2

5,7-Dimethyl-4-phenyl-6-(4-(piperidine-1-ylmethyl) phenyl)-2H-chromen-2-one example 2

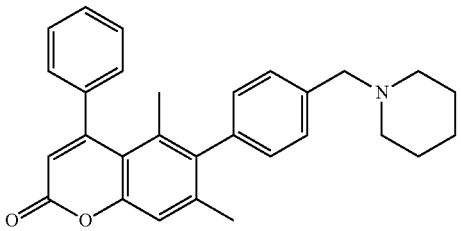

A mixture of 6-bromo-5,7-dimethyl-4-phenyl-2H-chromen-2-one (1-2) (99 mg, 0.30 mmol), 4-(bromomethyl) phenylboronic acid (97 mg, 0.45 mmol), piperidine (45 μL, 0.46 mmol), potassium carbonate (124 mg, 0.90 mmol) and Pd(dppf)$Cl_2$.$CH_2Cl_2$ (22 mg, 0.03 mmol) in a mixture of 1,4-dioxane and water (9:1, 3 mL) was stirred at 100° C. for 4 h. After cooled to room temperature, the mixture was partitioned between ethyl acetate and water. Organic phase was separated and dried over magnesium sulfate. Evaporation of the solvents give a residue, which was chromatographed on silica gel (EtOAc:hexanes=1:2-1:1) to give the title compound 2 (103 mg, 81% yield) as a yellow solid.

$^1$H NMR (300 MHz, $CDCl_3$) δ 7.45-7.36 (m, 3H), 7.36-7.27 (m, 4H), 7.21 (s, 1H), 6.98 (d, J=8.0, 2H), 6.24 (s, 1H), 3.48 (s, 2H), 2.38 (s, 4H), 2.08 (s, 3H), 1.66-1.52 (m, 4H), 1.49 (s, 3H), 1.47-1.37 (m, 2H).

MS (ESI) m/z 424 $(M+H)^+$.

Example 3

6-(4-((Cyclohexylamino)methyl)phenyl)-5,7-dimethyl-4-phenyl-2H-chromen-2-one example 3

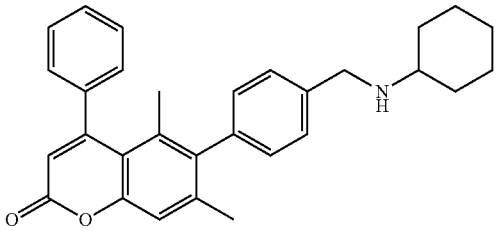

A mixture of 6-bromo-5,7-dimethyl-4-phenyl-2H-chromen-2-one (1-2) (99 mg, 0.30 mmol), 4-(bromomethyl) phenylboronic acid (97 mg, 0.45 mmol), cyclohexylamine (52 μL, 0.45 mmol), potassium carbonate (70 mg, 0.51 mmol) and Pd(dppf)$Cl_2$.$CH_2Cl_2$ (25 mg, 0.030 mmol) in a mixture of 1,4-dioxane and water (9:1, 3 mL) was stirred at 130° C. for 30 min under microwave irradiation. After cooled to room temperature, the mixture was diluted with ethyl acetate, filtered through a pad of Celite. The filtrate was washed with water and brine and dried over sodium sulfate. Evaporation of the solvents give a residue, which was chromatographed on silica gel (EtOAc:hexanes=1:1-2:1-1:0) to give the title compound 3 (79 mg, 60% yield) as a brown gum.

$^1$H NMR (300 MHz, $CDCl_3$) δ 7.46-7.27 (m, 7H), 7.21 (s, 1H), 7.00 (d, J=7.9, 2H), 6.24 (s, 1H), 3.83 (s, 2H), 2.60-2.41 (m, 1H), 2.07 (s, 3H), 2.00-1.86 (m, 2H), 1.84-1.66 (m, 2H), 1.67-1.55 (m, 2H), 1.49 (s, 5H), 1.36-0.99 (m, 7H).

Example 4

6-(4-((Hexylamino)methyl)phenyl)-5,7-dimethyl-4-phenyl-2H-chromen-2-one example 4

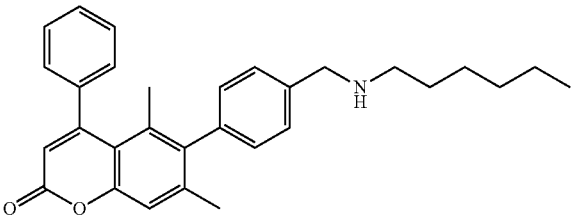

A mixture of 6-bromo-5,7-dimethyl-4-phenyl-2H-chromen-2-one (1-2) (99 mg, 0.30 mmol), 4-(bromomethyl) phenylboronic acid (97 mg, 0.45 mmol), 1-hexylamine (60 μL, 0.45 mmol), potassium carbonate (70 mg, 0.51 mmol) and Pd(dppf)$Cl_2$.$CH_2Cl_2$ (25 mg, 0.03 mmol) in a mixture of 1,4-dioxane and water (9:1, 3 mL) was stirred at 130° C. for 30 min under microwave irradiation. After cooled to room temperature, the mixture was diluted with ethyl acetate, filtered through a pad of Celite. The filtrate was washed with water and brine and dried over sodium sulfate. Evaporation of the solvents give a residue, which was chromatographed on silica gel (ethyl acetate:hexanes=1:1~2:1~1:0) to give the title compound 4 (44 mg, 33% yield) as a brown caramel.

$^1$H NMR (300 MHz, $CDCl_3$) δ 7.47-7.27 (m, 7H), 7.21 (s, 1H), 7.00 (d, J=8.0, 2H), 6.24 (s, 1H), 3.81 (s, 2H), 2.72-2.58 (m, 2H), 2.07 (s, 3H), 1.50 (m, 5H), 1.41-1.09 (m, 8H), 0.87 (t, J=6.8, 3H).

Example 5

5,7-Dimethyl-6-(4-((4-methylpiperazin-1-yl)methyl) phenyl)-4-phenyl-2H-chromen-2-one Example 5

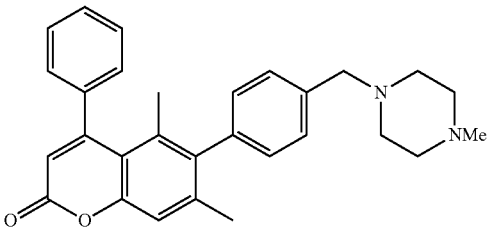

A mixture of 6-bromo-5,7-dimethyl-4-phenyl-2H-chromen-2-one (1-2) (99 mg, 0.30 mmol), 4-(bromomethyl) phenylboronic acid (97 mg, 0.45 mmol), 1-methyl-piperidine (50 μL, 0.45 mmol), potassium carbonate (70 mg, 0.51 mmol) and $Pd(dppf)Cl_2.CH_2Cl_2$ (25 mg, 0.03 mmol) in a mixture of 1,4-dioxane and water (9:1, 3 mL) was stirred at 130° C. for 30 min under microwave irradiation. After cooled to room temperature, the mixture was diluted with ethyl acetate, filtered through a pad of Celite. The filtrate was washed with water and brine and dried over sodium sulfate. Evaporation of the solvents give a residue, which was chromatographed on silica gel (0-5% methanol in chloroform) to give the title compound 5 (27 mg, 20% yield) as a brown gum.

$^1$H NMR (300 MHz, $CDCl_3$) δ 7.47-7.37 (m, 3H), 7.38-7.27 (m, 4H), 7.21 (s, 1H), 6.99 (d, J=8.0, 2H), 6.24 (s, 1H), 3.51 (s, 2H), 2.41 (brs, 8H), 2.29 (s, 3H), 2.04 (s, 3H), 1.49 (s, 3H).

Example 6

4-(3-Aminophenyl)-5,7-dimethyl-6-(4-(morpholinomethyl)phenyl)-2H-chromen-2-one hydrochloride example 6

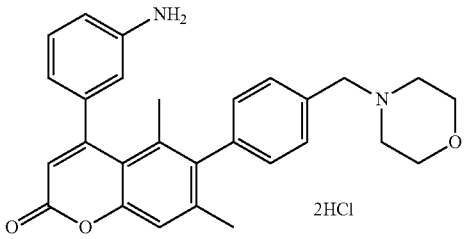

4-Bromo-3,5-dimethylphenyl propiolate (6-1)

6-1

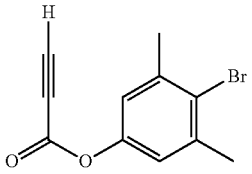

To a stirred solution of 4-bromo-3,5-dimethylphenol (40.87 g, 203.3 mmol) and propiolic acid (20.91 g, 298.5 mmol) in $CH_2Cl_2$ (400 mL) was added DCC (50.78 g, 246.1 mmol) in $CH_2Cl_2$ (100 mL) and DMAP (0.82 g, 6.7 mmol) at 0° C. The mixture was stirred at room temperature for 3 h and filtered. The filtrate was concentrated and purified by silica gel column chromatography (hexanes:EtOAc:$CH_2Cl_2$=20:1:10). The fractions containing the desired compound were concentrated. To the concentrate added hexane and the precipitated solid was collected by filtration. The solid was washed with hexane and dried to give the title compound 6-1 (26.12 g, 51% yield) as a white solid.

$^1$H NMR (300 MHz, $CDCl_3$) δ 6.89 (s, 2H), 3.08 (s, 1H), 2.42 (s, 6H).

4-Bromo-3,5-dimethylphenyl 3-(3-nitrophenyl)propiolate (6-2)

6-2

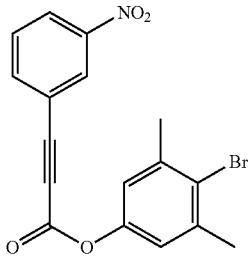

1-Iodo-3-nitrobenzene (41.05 g, 164.3 mmol) in THF (100 mL) was degassed under reduced pressure at −78° C., and then nitrogen gas was introduced. To the solution was added $K_2CO_3$ (41.27 g, 298.6 mmol), CuI (2.27 g, 11.9 mmol) and $PdCl_2(Ph_3P)_2$ (1.11 g, 1.57 mmol), and the mixture was stirred at 65° C. 4-bromo-3,5-dimethylphenyl propiolate (6-1) (37.79 g, 149.3 mmol) in THF (68 mL) was added by syringe pump over a period of 5.4 hr, and the mixture was stirred an additional 1 h after addition was complete. After being cooled to room temperature, the mixture was filtered. The filtrate was concentrated and purified by silica gel column chromatography. The fractions containing the desired compound were concentrated. To the concentrate added hexane and the precipitated solid was collected by filtration. The solid was washed with hexane and dried to give the title compound 6-2 (15.96 g, 29% yield) as a brown solid.

$^1$H NMR (300 MHz, $CDCl_3$) δ 8.49 (s, 1H), 8.35 (d, J=7.8, 1H), 7.94 (d, J=7.8, 1H), 7.64 (t, J=7.8, 1H), 6.94 (s, 2H), 2.44 (s, 6H).

6-Bromo-5,7-dimethyl-4-(3-nitrophenyl)-2H-chromen-2-one (6-3)

6-3

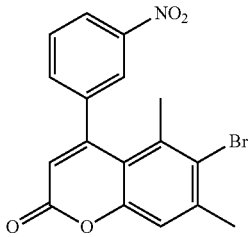

To a stirred solution of 4-bromo-3,5-dimethylphenyl 3-(3-nitrophenyl)propiolate (6-2) (15.96 g, 42.65 mmol) in $CH_2Cl_2$ (100 mL) was added TFA (10 mL) and $Pd(OAc)_2$ (480 mg, 2.14 mmol) at 0° C. The mixture was warmed to room temperature and stirred for 4.5 h. To the mixture was added 1,2-dichloroethane and concentrated. Then toluene was added and concentrated. To the concentrate added toluene, dichloromethane and hexane, and the precipitated solid was collected by filtration. The solid was washed with hexane and dried to give the title compound 6-3 (15.51 g, 97% yield) as a brown solid.

$^1$H NMR (300 MHz, $CDCl_3$) δ 8.35 (d, J=7.7, 1H), 8.19 (s, 1H), 7.70 (t, J=7.7, 1H), 7.65 (d, J=7.7, 1H), 7.24 (s, 1H), 6.31 (s, 1H), 2.54 (s, 3H), 1.95 (s, 3H).

MS (ESI) m/z 374 $(M+H)^+$.

4-(3-Aminophenyl)-6-bromo-5,7-dimethyl-2H-chromen-2-one (6-4)

6-4

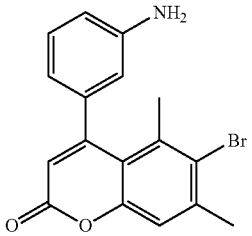

To a stirred solution of 6-bromo-5,7-dimethyl-4-(3-nitrophenyl)-2H-chromen-2-one (6-3) (15.41 g, 41.18 mmol) in EtOH (100 mL) and acetic acid (40 mL) was added iron (11.50 g, 205.9 mmol) at room temperature. The mixture was heated at 110° C. for 2 h. The reaction mixture was cooled at room temperature and filtrated. To the filtrate was added EtOAc and $Na_2CO_3$ (37 g, 0.35 mol) in water (200 mL). After being stirred at room temperature, the mixture was filtrated. Then the filtrated was diluted with EtOAc and extracted with EtOAc. The organic layers were washed with brine, dried over $Na_2SO_4$, and concentrated. To the concentrate added $CH_2Cl_2$-MeOH (1:9), and the precipitated solid was collected by filtration. The solid was washed with $CH_2Cl_2$-MeOH (1:9) and purified by silica gel column chromatography (hexanes:EtOAc=2:1~1:1) to give the title compound 6-4 (2.44 g, 17% yield) as a yellow solid.

$^1$H NMR (300 MHz, $CDCl_3$) δ 7.22 (t, J=7.9, 1H), 7.20 (s, 1H), 6.75 (d, J=7.9, 1H), 6.64 (d, J=7.9, 1H), 6.58 (s, 1H), 6.27 (s, 1H), 3.80 (s, 2H), 2.52 (s, 3H), 2.05 (s, 3H).

MS (ESI) m/z 344 $(M+H)^+$.

4-(3-Aminophenyl)-5,7-dimethyl-6-(4-(morpholinomethyl)phenyl)-2H-chromen-2-one (6-5)

6-5

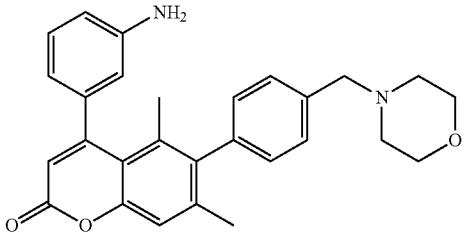

A mixture of 4-(3-aminophenyl)-6-bromo-5,7-dimethyl-2H-chromen-2-one (6-4) (25 mg, 0.073 mmol), 4-(bromomethyl)phenylboronic acid (24 mg, 0.11 mmol), morpholine (30 μL, 0.35 mmol), $K_2CO_3$ (18 mg, 0.13 mmol), dichloro(1,1'-bis(diphenylphosphino)ferrocene)palladium(II)-dichloromethane adduct (6 mg, 0.007 mmol), water (0.3 mL) and 1,4-dioxane (2.7 mL) was heated in a sealed vial in a microwave reactor at 130° C. for 30 min. To the mixture was added EtOAc and water, and extracted with EtOAc. The organic layers were washed with brine, dried over $Na_2SO_4$ and concentrated. The residue was purified by silica gel column chromatography (hexanes: EtOAc=1:1~0:1) to afford the title compound 6-5 (24 mg, 75% yield) as a yellow oil.

$^1$H NMR (300 MHz, $CDCl_3$) δ 7.35 (d, J=8.0, 2H), 7.19 (s, 1H), 7.16 (d, J=7.7, 1H), 7.00 (d, J=8.0, 2H), 6.71-6.63 (m, 2H), 6.60 (s, 1H), 6.24 (s, 1H), 3.77-3.69 (m, 6H), 3.52 (s, 2H), 2.48-2.42 (m, 4H), 2.07 (s, 3H), 1.59 (s, 3H).

MS (ESI) m/z 441 $(M+H)^+$.

4-(3-Aminophenyl)-5,7-dimethyl-6-(4-(morpholinomethyl)phenyl)-2H-chromen-2-one hydrochloride (example 6)

To a stirred solution of 4-(3-aminophenyl)-5,7-dimethyl-6-(4-(morpholinomethyl)phenyl)-2H-chromen-2-one (6-5) (290 mg, 0.658 mmol) in TBME (4 mL) was added hydrochloric acid (110 μL) in EtOH (0.1 mL) and TBME (3 mL) at 50° C. After being heated at 50° C. for 0.5 h, the mixture was stirred at room temperature for 1 h. Then the precipitated solid was collected by filtration and washed with TBME to give the title compound 6 (311 mg, 59% yield) as a yellow solid.

$^1$H NMR (300 MHz, $CD_3OD$) δ 7.66-7.56 (m, 3H), 7.44-7.37 (m, 2H), 7.35-7.25 (m, 4H), 6.27 (s, 1H), 4.42 (s, 2H), 4.10-4.01 (m, 2H), 3.82-3.70 (m, 2H), 3.44-3.37 (m, 2H), 3.26-3.20 (m, 2H), 2.08 (s, 3H), 1.54 (s, 3H).

Example 7

4-(4-Aminophenyl)-5,7-dimethyl-6-(4-(morpholinomethyl)phenyl)-2H-chromen-2-one example 7

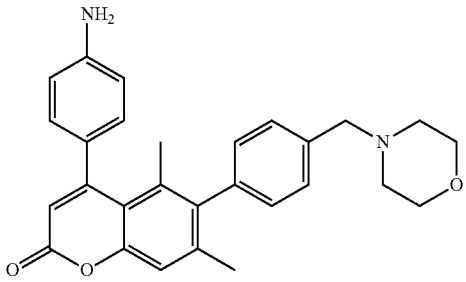

4-Bromo-3,5-dimethylphenyl 3-(4-nitrophenyl)propiolate (7-1)

7-1

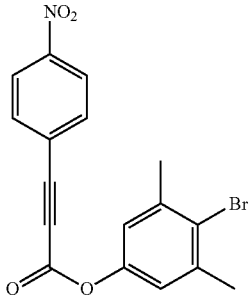

1-Iodo-4-nitrobenzene (550 mg, 2.17 mmol) in THF (4 mL) was degassed under reduced pressure at −78° C., and then nitrogen gas was introduced. To the solution was added $K_2CO_3$ (552 mg, 298.6 mmol), CuI (30 mg, 0.16 mmol) and $PdCl_2(Ph_3P)_2$ (14 mg, 0.020 mmol), and the mixture was stirred at 65° C. 4-bromo-3,5-dimethylphenyl propiolate (6-1) (506 mg, 2.03 mmol) in THF (2.5 mL) was added by syringe pump over a period of 6 h. After being cooled to room temperature, the mixture was filtered and washed with EtOAc. The filtrate was concentrated and purified by silica gel column chromatography to give the title compound 7-1 (551 mg, 74% yield) as a brown solid.

$^1$H NMR (300 MHz, $CDCl_3$) δ 8.29 (d, J=8.7, 2H), 7.81 (d, J=8.7, 2H), 6.94 (s, 2H), 2.44 (s, 6H).

6-Bromo-5,7-dimethyl-4-(4-nitrophenyl)-2H-chromen-2-one (7-2)

4-(4-Aminophenyl)-6-bromo-5,7-dimethyl-2H-chromen-2-one (7-3)

7-2

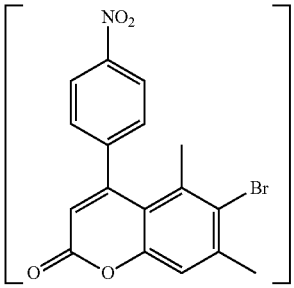

7-3

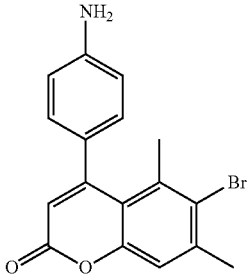

To a stirred solution of 4-bromo-3,5-dimethylphenyl 3-(4-nitrophenyl)propiolate (7-1) (524 mg, 1.40 mmol) in $CH_2Cl_2$ (8 mL) was added TFA (0.8 mL) and $Pd(OAc)_2$ (16 mg, 0.071 mmol) at 0° C. The mixture was warmed to room temperature and stirred for 3.5 h. To the mixture was added 1,2-dichloroethane and concentrated. Then to the concentrate were added $CHCl_3$, DMSO and EtOH, and filtrated. The filtrate was concentrated and purified by silica gel column chromatography to afford the crude material (22 mg) containing compound 7-2.

To a stirred solution of the crude material (22 mg) containing 6-bromo-5,7-dimethyl-4-(4-nitrophenyl)-2H-chromen-2-one (7-2) in EtOH (0.75 mL) and acetic acid (0.15 mL) was added iron (16 mg, 0.29 mmol) at room temperature. The mixture was heated at 110° C. for 2.5 h. The reaction mixture was then cooled at room temperature and filtrated. To the filtrate was added EtOAc and saturated $NaHCO_3$ solution, and extracted with EtOAc. The organic layers were washed with brine, dried over $Na_2SO_4$ and concentrated. The residues was purified by silica gel column chromatography (hexane:EtOAc=5:1~2:1) to give the title compound 7-3 (4.0 mg, 0.8% yield, 2 steps) as an orange solid.

$^1$H NMR (300 MHz, $CDCl_3$) δ 7.19 (s, 1H), 7.08 (d, J=8.4, 2H), 6.74 (d, J=8.4, 2H), 6.24 (s, 1H), 3.89 (s, 2H), 2.52 (s, 3H), 2.06 (s, 3H).

MS (ESI) m/z 344 $(M+H)^+$.

4-(4-Aminophenyl)-5,7-dimethyl-6-(4-(morpholinomethyl)phenyl)-2H-chromen-2-one (example 7)

A mixture of 4-(4-aminophenyl)-6-bromo-5,7-dimethyl-2H-chromen-2-one (7-3) (4 mg, 0.01 mmol), 4-(bromomethyl)phenylboronic acid (4 mg, 0.02 mmol), morpholine (4.7 μL, 0.054 mmol), potassium carbonate (3 mg, 0.02 mmol), dichloro(1,1'-bis(diphenylphosphino)ferrocene)palladium(II)-dichloromethane adduct (1 mg, 0.001 mmol), water (0.2 mL) and 1,4-dioxane (1.8 mL) was heated in a sealed vial in a microwave reactor at 130° C. for 30 min. To the mixture was added EtOAc and water, and extracted with EtOAc. The organic layers were combined, washed with brine, dried over $Na_2SO_4$ and concentrated. The residue was purified by silica gel column chromatography (hexanes: EtOAc=5:5~0:1), and then purified by preparative TLC to afford the title compound 7 (2.3 mg, 43% yield) as a yellow oil.

$^1$H NMR (300 MHz, $CDCl_3$) δ 7.36 (d, J=8.0, 2H), 7.18 (s, 1H), 7.08 (d, J=8.5, 2H), 7.02 (d, J=8.0, 2H), 6.70 (d, J=8.5, 2H), 6.22 (s, 1H), 3.81 (s, 2H), 3.75-3.70 (m, 4H), 3.53 (s, 2H), 2.49-2.43 (m, 4H), 2.07 (s, 3H).

MS (ESI) m/z 441 $(M+H)^+$.

Example 8

5,7-Dimethyl-6-(4-(morpholinomethyl)phenyl)-4-(3-nitrophenyl)-2H-chromen-2-one example 8

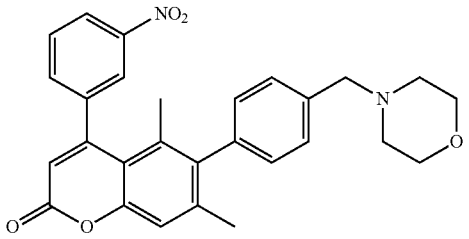

A mixture of 6-bromo-5,7-dimethyl-4-(3-nitrophenyl)-2H-chromen-2-one (6-3) (27 mg, 0.073 mmol), 4-(bromomethyl)phenylboronic acid (24 mg, 0.11 mmol), morpholine (10 μL, 0.12 mmol), potassium carbonate (18 mg, 0.13 mmol), dichloro(1,1'-bis(diphenylphosphino)ferrocene)palladium(II)-dichloromethane adduct (6 mg, 0.007 mmol), water (0.3 mL) and 1,4-dioxane (2.7 mL) was heated in a sealed vial in a microwave reactor at 130° C. for 30 min. To the mixture was added EtOAc and water, and extracted with EtOAc. The organic layers were combined, washed with brine, dried over $MgSO_4$ and concentrated. The residue was purified by silica gel column chromatography (hexanes: EtOAc=2:1~1:1~0:1) to afford the title compound 8 (15 mg, 44% yield) as a yellow oil.

$^1$H NMR (300 MHz, $CDCl_3$) δ 8.31-8.26 (m, 1H), 8.22-8.21 (m, 1H), 7.71-7.64 (m, 2H), 7.36 (d, J=7.2, 2H), 7.25 (s, 1H), 7.04-6.96 (m, 2H), 6.26 (s, 1H), 3.73-3.69 (m, 4H), 3.52 (s, 2H), 2.48-2.42 (m, 4H), 2.09 (s, 3H), 1.47 (s, 3H).

MS (ESI) m/z 471 $(M+H)^+$.

Example 9

Methyl 3-(5,7-dimethyl-6-(4-(morpholinomethyl) phenyl)-2-oxo-2H-chromen-4-yl)benzoate example 9

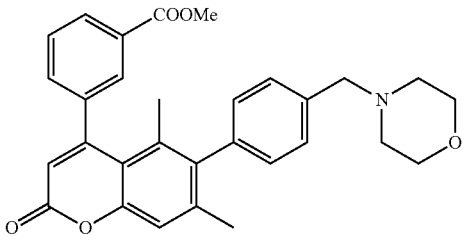

Methyl 3-(3-(tert-butoxy)-3-oxoprop-1-yn-1-yl)benzoate (9-1)

9-1

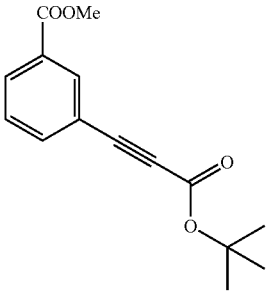

To the mixture of methyl 3-iodobenzoate (157 mg, 0.60 mmol), potassium carbonate (166 mg, 1.20 mmol), cupper(I) iodide (14 mg, 0.07 mmol) and $PdCl_2(Ph_3P)_2$ (21 mg, 0.03 mmol) in tetrahydrofuran (2 mL) was added tert-butyl propiolate (330 μL, 2.40 mmol) at room temperature. After stirred for 20 h at 60° C., the mixture was evaporated to dryness. The residue was chromatographed on a silica gel (EtOAc:hexanes=0:1~1:10) to give the title compound 9-1 (155 mg, 99% yield) as a light brown oil.

$^1$H NMR (300 MHz, $CDCl_3$) δ 8.25 (t, J=1.4, 1H), 8.16-8.05 (m, 1H), 7.80-7.68 (m, 1H), 7.46 (t, J=7.8, 1H), 3.93 (s, 3H), 1.55 (s, 9H).

3-(3-(Methoxycarbonyl)phenyl)propiolic acid (9-2)

9-2

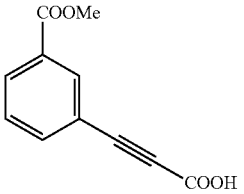

The mixture of methyl 3-(3-(tert-butoxy)-3-oxoprop-1-yn-1-yl)benzoate (9-1) (139 mg, 0.53 mmol) in a mixture of trifluoroacetic acid and dichloromethane (v:v=95:5, 1.5 mL) was stirred at room temperature for 2 h. The mixture was diluted with 1,2-dichloroethane and the whole was evaporated to dryness. The residue was triturated with hexane and the solid was collected by decantation and dried under vacuum to give the title compound 9-2 (102 mg, 94% yield) as a light brown solid.

$^1$H NMR (300 MHz, DMSO-$d_6$) δ 8.16-8.02 (m, 2H), 7.91 (dt, J=7.7, 1.3, 1H), 7.64 (t, J=7.7, 1H), 3.88 (s, 3H).

$^{13}$C NMR (75 MHz, DMSO-$d_6$) δ 165.12, 154.00, 136.87, 132.86, 131.21, 130.44, 129.79, 119.62, 82.87, 82.31, 52.51.

Methyl 3-(3-(4-bromo-3,5-dimethylphenoxy)-3-oxoprop-1-yn-1-yl)benzoate (9-3)

9-3

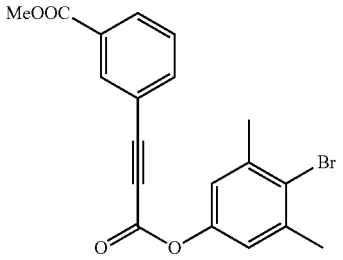

To a stirring solution of 3-(3-methoxycarbonylphenyl) propiolic acid (9-2) (102 mg, 0.50 mmol), 4-bromo-3,5-dimethylphenol (103 mg, 0.51 mmol) and 4-(dimethylamino)pyridine (12 mg, 0.10 mmol) in dichloromethane (2 mL) was added a solution of DCC (114 mg, 0.55 mmol) in dichloromethane (1 mL) under ice-cooling. The mixture was stirred under ice-cooling for 30 min then stirred at room temperature for 18 h. The mixture was diluted with dichloromethane filtered through a pad of Celite. The filtrate was evaporated to dryness, which was chromatographed on a silica gel (dichloromethane:hexanes=2:3) to give title compound 9-3 (95 mg, 49% yield) as a white solid.

$^1$H NMR (300 MHz, $CDCl_3$) δ 8.31 (t, J=1.4, 1H), 8.22-8.07 (m, 1H), 7.87-7.71 (m, 1H), 7.51 (t, J=7.8, 1H), 6.94 (s, 2H), 3.95 (s, 3H), 2.43 (s, 6H).

Methyl 3-(6-bromo-5,7-dimethyl-2-oxo-2H-chromen-4-yl)benzoate (9-4)

9-4

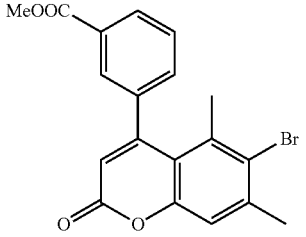

To a stirring solution of methyl 3-(3-(4-bromo-3,5-dimethylphenoxy)-3-oxoprop-1-yn-1-yl)benzoate (9-3) (95 mg, 0.25 mmol) in dichloromethane (1 mL) and trifluoroacetic acid (2 mL) was added palladium acetate (5 mg, 0.02 mmol) under ice-cooling. After stirred for 3 h under ice-cooling, the mixture was diluted with 1,2-dichloromethane and evaporated to dryness. Chromatography of the residue on a silica gel (chloroform:hexanes=1:1-1:0) gave title compound 9-4 (69 mg, 73% yield) as a light brown gum.

$^1$H NMR (300 MHz, $CDCl_3$) δ 8.15 (dt, J=7.7, 1.4, 1H), 7.99 (t, J=1.7, 1H), 7.57 (t, J=7.7, 1H), 7.49 (dt, J=7.7, 1.5, 1H), 7.23 (s, 1H), 6.28 (s, 1H), 3.95 (s, 3H), 2.53 (s, 3H), 1.94 (s, 3H).

Methyl 3-(5,7-dimethyl-6-(4-(morpholinomethyl) phenyl)-2-oxo-2H-chromen-4-yl)benzoate (example 9)

A mixture of methyl 3-(6-bromo-5,7-dimethyl-2-oxo-2H-chromen-4-yl)benzoate (9-4) (63 mg, 0.16 mmol), 4-(bromomethyl)phenylboronic acid (51 mg, 0.24 mmol), morpholine (21 μL, 0.24 mmol), potassium carbonate (37 mg, 0.27 mmol), dichloro(1,1'-bis(diphenylphosphino)ferrocene)palladium(II)-dichloromethane adduct (13 mg, 0.016 mmol), water (0.3 mL) and 1,4-dioxane (2.7 mL) was heated in a sealed vial in a microwave reactor at 130° C. for 30 min. To the mixture was added EtOAc and water, and extracted with EtOAc. The organic layers were combined, washed with saturated $NaHCO_3$ solution and brine, dried over $Na_2SO_4$ and concentrated. The residue was purified by silica gel column chromatography (hexanes: EtOAc=4:1→3:2→1:1) to afford the title compound 9 (41 mg, 53% yield) as a foam.

$^1$H NMR (300 MHz, $CDCl_3$) δ 8.08 (s, 1H), 8.01 (s, 1H), 7.51 (s, 2H), 7.35 (d, J=7.8, 2H), 7.23 (s, 1H), 7.05-6.96 (m, 2H), 6.24 (s, 1H), 3.93 (s, 3H), 3.72 (s, 4H), 3.52 (s, 2H), 2.45 (s, 4H), 2.08 (s, 3H), 1.46 (s, 3H).

MS (ESI) m/z 484 $(M+H)^+$.

Example 10

N-(3-(5,7-dimethyl-6-(4-(morpholinomethyl)phenyl)-2-oxo-2H-chromen-4-yl)phenyl)acetamide example 10

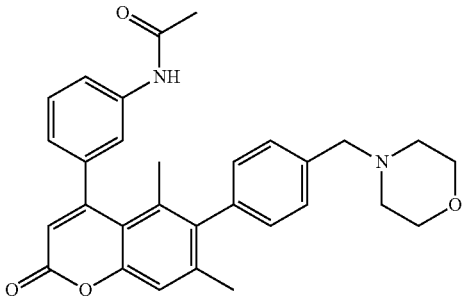

To a stirred solution of 4-(3-aminophenyl)-5,7-dimethyl-6-(4-(morpholinomethyl)phenyl)-2H-chromen-2-one (6-5) (14 mg, 0.03 mmol) and $Et_3N$ (21 μL, 0.15 mmol) in $CH_2Cl_2$ (1.5 mL) was added acetyl chloride (3 μL) at room temperature. After being stirred at room temperature for 2 h, to the mixture was added acetyl chloride (2 μL). Then the mixture was stirred at room temperature for 0.5 h. The mixture was diluted with EtOAc and brine, and then extracted with EtOAc. The combined organic layers were dried over $Na_2SO_4$ and concentrated. The residue was purified by silica gel column chromatography (EtOAc: MeOH=10:0~9:1~8:2) to afford the title compound 10 (15 mg, quantitative yield) as a colorless oil.

$^1$H NMR (300 MHz, $CDCl_3$) δ 7.58 (s, 1H), 7.44 (d, J=7.2, 1H), 7.38-7.32 (m, 4H), 7.23-7.19 (m, 2H), 7.06-6.98 (m, 3H), 6.23 (s, 1H), 3.73-3.69 (m, 4H), 3.52 (s, 2H), 2.47-2.43 (m, 4H), 2.19 (s, 3H), 2.07 (s, 3H), 1.55 (s, 3H).

MS (ESI) m/z 483 $(M+H)^+$.

Example 11

N-(3-(5,7-dimethyl-6-(4-(morpholinomethyl)phenyl)-2-oxo-2H-chromen-4-yl)phenyl)methanesulfonamide example 11

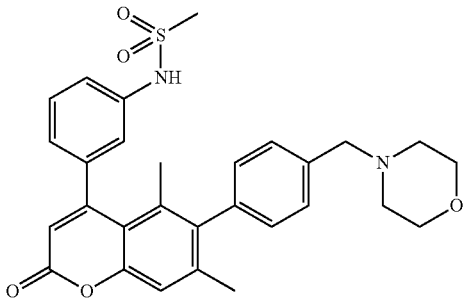

To a stirred solution of 4-(3-aminophenyl)-5,7-dimethyl-6-(4-(morpholinomethyl)phenyl)-2H-chromen-2-one (6-5) (10 mg, 0.023 mmol) and pyridine (18 μL) in $CH_2Cl_2$ (1.0 mL) was added methanesulfonyl chloride (3 μL) at room temperature. After being stirred at room temperature for 1 h, to the mixture was added additional methanesulfonyl chloride (6 μL). Then the mixture was stirred at room temperature for 2.7 h. The mixture was diluted with brine, and extracted with $CH_2Cl_2$. The combined organic layers were concentrated. The residue was purified by silica gel column chromatography (hexanes:EtOAc:MeOH=5:5:0→0:10:0→0:9:1→0:8:2) to afford the title compound 11 (6 mg, 50% yield) as a yellow oil.

$^1$H NMR (300 MHz, $CDCl_3$) δ 7.45-7.34 (m, 3H), 7.22-7.12 (m, 3H), 7.05-6.98 (m, 2H), 6.55 (s, 1H), 6.24 (s, 1H), 3.78-3.70 (m, 4H), 3.55 (s, 2H), 3.04 (s, 3H), 2.54-2.44 (m, 4H), 2.08 (s, 3H), 1.54 (s, 3H).

MS (ESI) m/z 519 $(M+H)^+$.

Example 12

Ethyl (3-(5,7-dimethyl-6-(4-(morpholinomethyl) phenyl)-2-oxo-2H-chromen-4-yl)phenyl)carbamate example 12

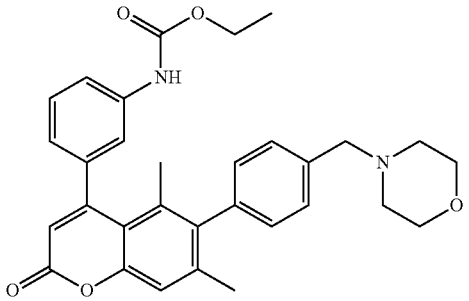

To a stirred solution of 4-(3-aminophenyl)-5,7-dimethyl-6-(4-(morpholinomethyl)phenyl)-2H-chromen-2-one (6-5) (10 mg, 0.023 mmol) and pyridine (18 μL) in $CH_2Cl_2$ (1.0 mL) was added ethyl chloroformate (3 μL) at room temperature. After being stirred at room temperature for 1 h, the mixture was diluted with brine, and then extracted with $CH_2Cl_2$. The combined organic layers were concentrated. The residue was purified by silica gel column chromatography (hexanes:EtOAc=5:5→0:10) to afford the title compound 12 (9 mg, 76% yield) as a yellow oil.

$^1$H NMR (300 MHz, $CDCl_3$) δ 7.45 (s, 1H), 7.37-7.32 (m, 4H), 7.20 (s, 1H), 7.05-6.98 (m, 3H), 6.63 (s, 1H), 6.24 (s, 1H), 4.22 (d, J=7.2, 2H), 3.74-3.69 (m, 4H), 3.52 (s, 2H), 2.48-2.43 (m, 4H), 2.07 (s, 3H), 1.54 (s, 3H), 1.30 (d, J=7.2, 3H).

MS (ESI) m/z 513 $(M+H)^+$.

Example 13

5,7-Dimethyl-6-(4-(morpholinomethyl)phenyl)-4-(pyridin-3-yl)-2H-chromen-2-one example 13

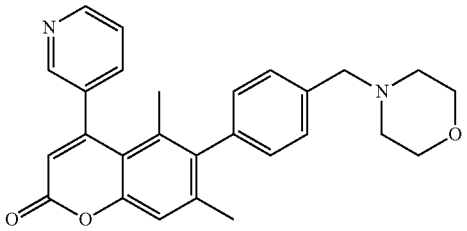

4-Bromo-3,5-dimethylphenyl 3-(pyridin-3-yl)propiolate (13-1)

13-1

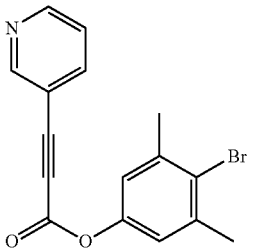

3-Iodopyridine (226 mg, 1.10 mmol) in THF (2 mL) was degassed under reduced pressure at −78° C., and then nitrogen gas was introduced. To the solution was added $K_2CO_3$ (276 mg, 2.00 mmol), CuI (15 mg, 0.079 mmol) and $PdCl_2(Ph_3P)_2$ (7 mg, 0.01 mmol), and the mixture was stirred at 65° C. 4-bromo-3,5-dimethylphenyl propiolate (6-1) (253 mg, 1.00 mmol) in THF (2 mL) was added by syringe pump over a period of 5 h, and the mixture was stirred an additional 1 h after addition was complete. After being cooled to room temperature, the mixture was filtered. The filtrate was concentrated and purified by silica gel column chromatography to give the title compound 13-1 (88 mg, 27% yield) as a black oil.

$^1$H NMR (300 MHz, $CDCl_3$) δ 8.86 (s, 1H), 8.71 (dd, J=1.4, 4.9, 1H), 7.93 (dt, J=1.4, 7.9, 1H), 7.38 (ddd, J=0.8, 4.9, 7.9, 1H), 6.94 (s, 2H), 2.44 (s, 6H).

MS (ESI) m/z 331 $(M+H)^+$.

6-Bromo-5,7-dimethyl-4-(pyridin-3-yl)-2H-chromen-2-one (13-2)

5,7-Dimethyl-6-(4-(morpholinomethyl)phenyl)-4-(pyridin-3-yl)-2H-chromen-2-one (example 13)

13-2

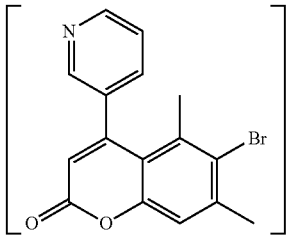

To a stirred solution of 4-bromo-3,5-dimethylphenyl 3-(pyridin-3-yl)propiolate (13-1) (87 mg, 0.26 mmol) in $CH_2Cl_2$ (1 mL) was added TFA (0.1 mL) and $Pd(OAc)_2$ (3 mg, 0.01 mmol) at 0° C. The mixture was warmed to room temperature and stirred for 1.3 h. To the mixture was added TFA (0.9 mL) and $Pd(OAc)_2$ (30 mg, 0.13 mmol), and stirred for 2 h. To the mixture was added 1,2-dichloroethane and concentrated. Then to the concentrate was added EtOAc and saturated $NaHCO_3$ solution, and the precipitated solid was collected by filtration.

The solid was washed with EtOAc and the filtrate was extracted with EtOAc. The organic layers were washed with brine, dried over $Na_2SO_4$ and concentrated. The residue was combined with the solid to afford the crude material containing compound 13-2.

A mixture of the crude material containing 6-bromo-5,7-dimethyl-4-(pyridin-3-yl)-2H-chromen-2-one (13-2), 4-(bromomethyl)phenylboronic acid (84 mg, 0.39 mmol), morpholine (101 μL, 1.17 mmol), $K_2CO_3$ (65 mg, 0.47 mmol), dichloro(1,1'-bis(diphenylphosphino)ferrocene)palladium(II)-dichloromethane adduct (21 mg, 0.026 mmol), water (0.2 mL) and 1,4-dioxane (1.8 mL) was heated in a sealed vial in a microwave reactor at 130° C. for 30 min. To the mixture was added EtOAc and water, and extracted with EtOAc. The organic layers were combined, washed with brine, dried over $Na_2SO_4$ and concentrated. The residue was purified by silica gel column chromatography (hexanes: EtOAc=5:5→0:1). The fractions containing the desired compound were pooled and concentrated. To the concentrate was added aqueous 1N HCl, TBME and PhMe, and extracted with aqueous 1N HCl. The aqueous layers were added water, brine and $CH_2Cl_2$, and extracted with $CH_2Cl_2$ and EtOAc. The organic layers were concentrated and then purified by preparative TLC to afford the title compound 13 (1.4 mg, 1.3% yield, 2 steps) as a yellow oil.

$^1$H NMR (300 MHz, $CDCl_3$) δ 8.67 (d, J=4.0, 1H), 8.60 (s, 1H), 7.66 (d, J=7.8, 1H), 7.41-7.33 (m, 3H), 7.24 (s, 1H), 7.00 (d, J=6.7, 2H), 6.26 (s, 1H), 3.77-3.68 (m, 4H), 3.53 (s, 2H), 2.50-2.41 (m, 4H), 2.09 (s, 3H), 1.51 (s, 3H).

MS (ESI) m/z 427 $(M+H)^+$.

Example 14

The antitubercular activity was evaluated against Mtb strain H37Rv. The inhibitory activity ($IC_{90}$) of the compounds is reported in Table A.

$IC_{90}$ was determined using an OD600 based assay. Bacteria were grown to mid-log phase and plated in 96 well plates at OD600=0.025 in the presence of small molecule inhibitors. Bacteria were incubated in sealed Tupperware containers for 7 days, and growth was assessed by reading OD600. The $IC_{90}$ was defined as the concentration of inhibitor which resulted in 90% inhibition of growth of the control. For $IC_{99}$ determinations, cultures were set up as described above, however plates were incubated for a total of 14 days at which time cultures were harvested and plated on agar plates for enumeration of CFU. The $IC_{99}$ was determined as the concentration of inhibitor that resulted in 99% inhibition of growth relative to the DMSO control.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of Formula Ia or a pharmaceutically acceptable salt thereof:

Formula Ia

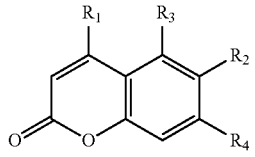

wherein:

$R_1$ is selected from the group consisting of phenyl, substituted phenyl, pyridinyl, and substituted pyridinyl;

$R_3$ is hydrogen or unsubstituted $C_1$-$C_8$ alkyl;

$R_4$ is hydrogen or unsubstituted $C_1$-$C_8$ alkyl;

$R_2$ is:

[ 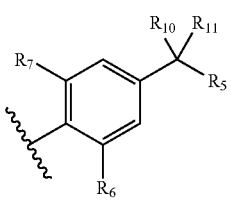 ]

-continued

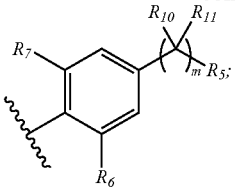

each $R_6$, $R_7$, $R_{10}$ and $R_{11}$ is independently selected from the group consisting of hydrogen and unsubstituted $C_1$-$C_8$ alkyl;

*m is 0;*

$R_5$ is selected from the group consisting of:

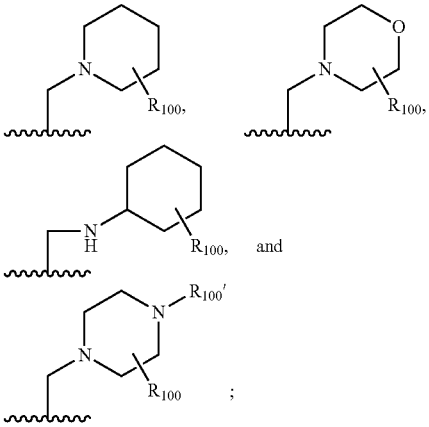

$R_{100}$ is hydrogen or unsubstituted $C_1$-$C_8$ alkyl; and $R_{100}'$ is hydrogen or unsubstituted $C_1$-$C_8$ alkyl;

wherein the substituted phenyl and the substituted pyridinyl are each independently substituted with one or more substituents independently selected from the group consisting of halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl,[-alkoxy] *alkoxy*, aryloxy, aralkoxy, aminocarbonyl, alkylaminocarbonyl, arylaminocarbonyl,[-alkoxycarbonyl] *alkoxycarbonyl*, aryloxycarbonyl, haloalkyl, amino, cyano, nitro, alkylamino, arylamino, alkylaminoalkyl, arylaminoalkyl, aminoalkylamino, hydroxy, alkoxyalkyl, carboxy, carboxyalkyl, alkoxycarbonylalkyl, aminocarbonylalkyl, acyl, aralkoxycarbonyl, and sulfonyl.

2. The compound [of claim 1] selected from the group consisting of:

4-(3-aminophenyl)-5,7-dimethyl-6-(4-(morpholinomethyl)phenyl)-2H-chromen-2-one; and 4-phenyl-5,7-dimethyl-6-(4-(morpholinomethyl)phenyl)-2H-chromen-2-one, or a pharmaceutically acceptable salt of any of thereof.

3. The compound of claim 1, wherein $R_5$ is selected from the group consisting of:

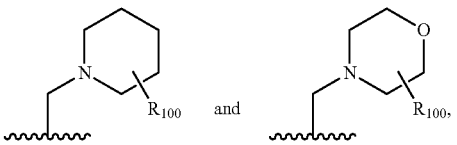

or a pharmaceutically acceptable salt thereof.

4. The compound of claim 1, wherein $R_3$ is unsubstituted $C_1$-$C_8$ alkyl, and $R_4$ is unsubstituted $C_1$-$C_8$ alkyl, or a pharmaceutically acceptable salt thereof.

5. The compound of claim 1, wherein $R_1$ is phenyl or substituted phenyl, or a pharmaceutically acceptable salt thereof.

6. A pharmaceutical composition comprising a pharmaceutically acceptable carrier and the compound of claim 1, or a pharmaceutically acceptable salt thereof.

7. A compound selected from the table below, or a pharmaceutically acceptable salt thereof:

TABLE A

| No | Structure |
|---|---|
| 1 | 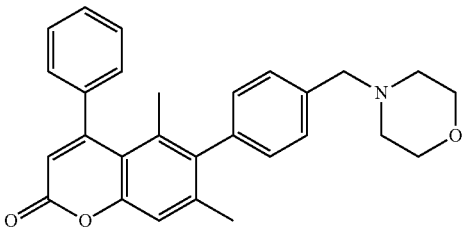 5,7-dimethyl-6-(4-(morpholinomethyl)phenyl)-4-phenyl-2H-chromen-2-one |
| 2 | 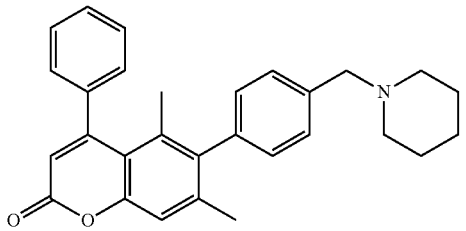 5,7-dimethyl-4-phenyl-6-(4-(piperidin-l-ylmethyl)phenyl)-2H-chromen-2-one |
| 3 | 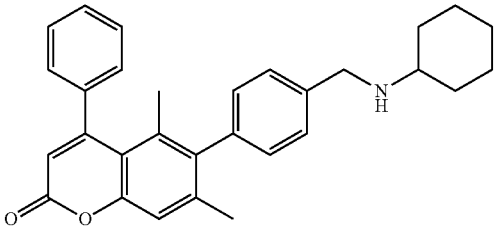 6-(4-((cyclohexylamino )methyl)phenyl)-5,7-dimethyl-4-phenyl-2H-chromen-2-one |
| 5 | 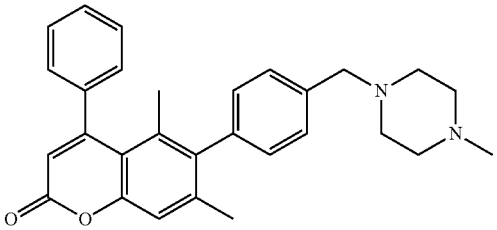 5,7-dimethyl-6-(4-((4-methylpiperazin-1-yl)methyl)phenyl)-4-phenyl-2H-chromen-2-one |

TABLE A-continued

| No | Structure |
|---|---|
| 6 | 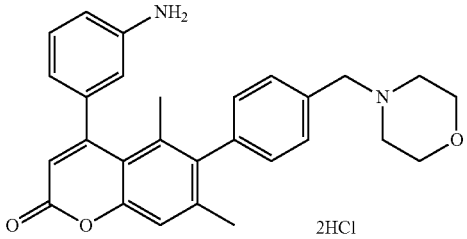 4-(3-aminophenyl)-5,7-dimethyl-6-(4-(morpholinomethyl)phenyl)-2H-chromen-2-one hydrochloride |
| 7 | 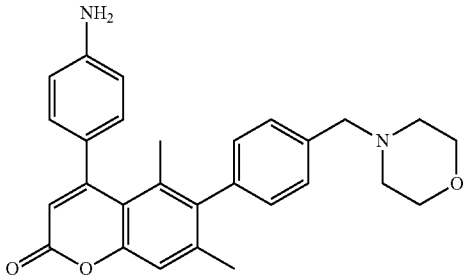 4-(4-aminophenyl)-5,7-dimethyl-6-(4-(morpholinomethyl)phenyl)-2H-chromen-2-one |
| 8 | 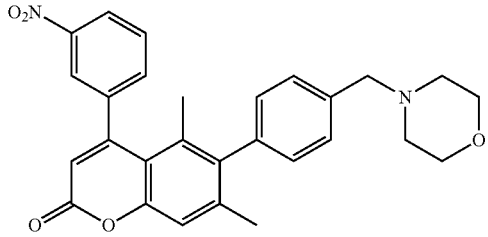 5,7-dimethyl-6-(4-(morpholinomethyl)phenyl)-4-(3-nitrophenyl)-2H-chromen-2-one |
| 9 | 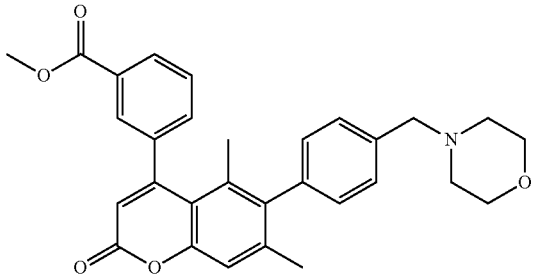 methyl 3-(5,7-dimethyl-6-(4-(morpholinomethyl)phenyl)-2-oxo-2H-chromen-4-yl)benzoate |
| 10 | 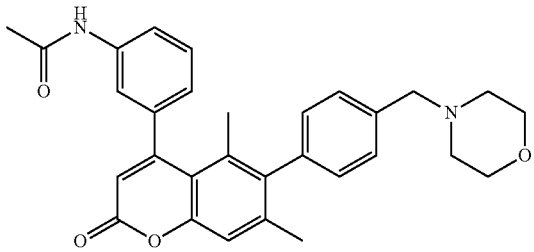 N-(3-(5,7-dimethyl-6-(4-(morpholinomethyl)phenyl)-2-oxo-2H-chromen-4-yl)phenyl)acetamide |

TABLE A-continued

| No | Structure |
|---|---|
| 11 | 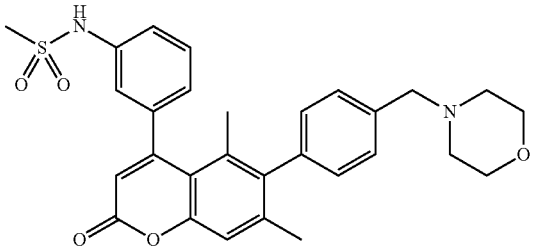 N-(3-(5,7-dimethyl-6-(4-(morpholinomethyl)phenyl)-2-oxo-2H-chromen-4-yl)phenyl)methanesulfonamide |
| 12 | 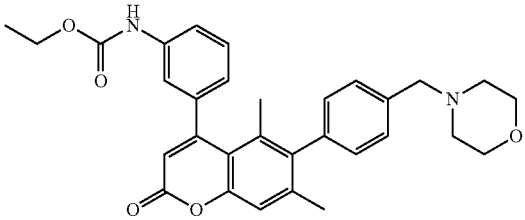 ethyl (3-(5,7-dimethyl-6-(4-(morpholinomethyl)phenyl)-2-oxo-2H-chromen-4-yl)phenyl)caxbamate |
| 13 | 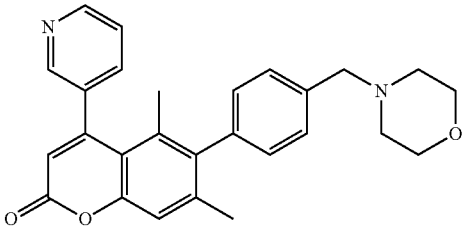 5,7-dimethyl-6-(4-(morpholinomethyl)phenyl)-4-(pyridin-3-yl)-2H-chromen-2-one |
| 43 | 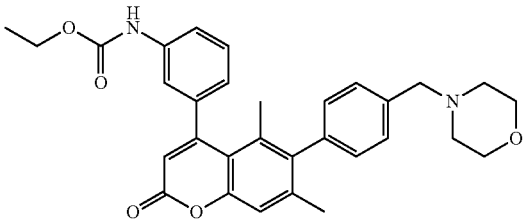 |
| 44 | 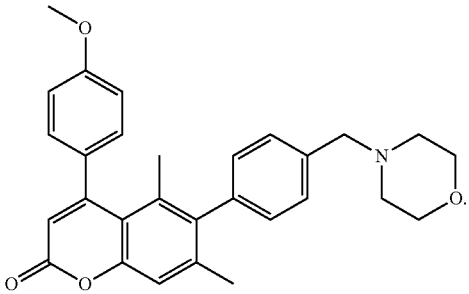 |

8. The compound of claim 1, wherein $R_5$ is:

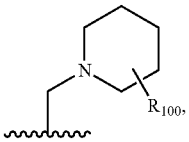

or a pharmaceutically acceptable salt thereof.

9. The compound of claim 1, wherein $R_5$ is:

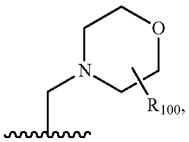

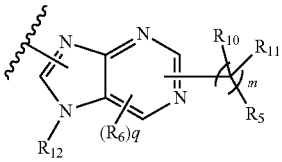

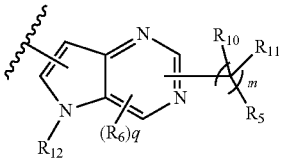

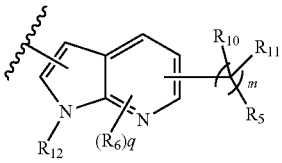

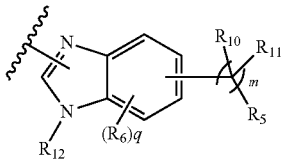

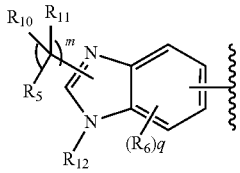

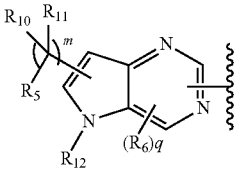

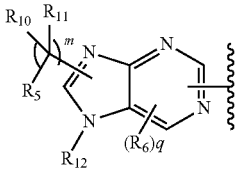

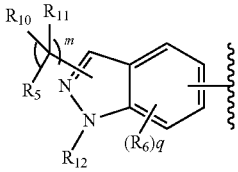

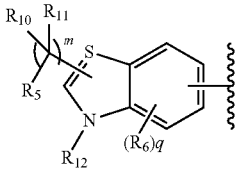

-continued

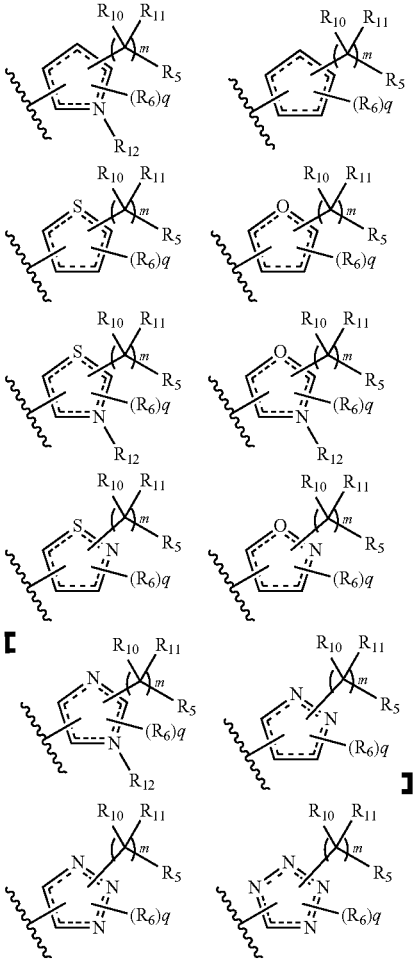

or a pharmaceutically acceptable salt thereof.

10. The compound of claim 1, wherein $R_5$ is:

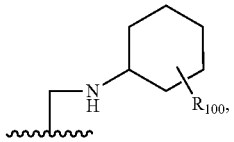

or a pharmaceutically acceptable salt thereof.

11. The compound of claim 1, wherein $R_5$ is:

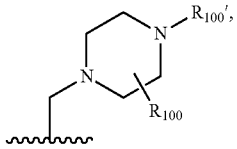

or a pharmaceutically acceptable salt thereof.

12. The compound of claim 8, wherein $R_{100}$ is hydrogen, or a pharmaceutically acceptable salt thereof.

13. The compound of claim 9, wherein $R_{100}$ is hydrogen, or a pharmaceutically acceptable salt thereof.

14. The compound of claim 10, wherein $R_{100}$ is hydrogen, or a pharmaceutically acceptable salt thereof.

15. The compound of claim 11, wherein $R_{100}$ is hydrogen, or a pharmaceutically acceptable salt thereof.

16. The compound of claim 15, wherein $R_{100'}$ is hydrogen or methyl, or a pharmaceutically acceptable salt thereof.

17. The compound of claim 4, wherein $R_3$ is unsubstituted $C_1$-$C_3$ alkyl, and $R_4$ is unsubstituted $C_1$-$C_3$ alkyl, or a pharmaceutically acceptable salt thereof.

18. The compound of claim 17, wherein $R_3$ is methyl and $R_4$ is methyl, or a pharmaceutically acceptable salt thereof.

19. A pharmaceutical composition comprising a pharmaceutically acceptable carrier and a compound of claim 7, or a pharmaceutically acceptable salt thereof.

* * * * *